US010067565B2

United States Patent
Ramaprakash et al.

(10) Patent No.: US 10,067,565 B2
(45) Date of Patent: Sep. 4, 2018

(54) METHODS AND APPARATUS FOR IDENTIFYING POTENTIALLY SEIZURE-INDUCING VIRTUAL REALITY CONTENT

(71) Applicant: Intel Corporation, Santa Clara, CA (US)

(72) Inventors: Nishanth Ramaprakash, Bangalore (IN); Sreenidhi Koti Ananda Rao, Bangalore (IN)

(73) Assignee: Intel Corporation, Santa Clara, CA (US)

( * ) Notice: Subject to any disclaimer, the term of this patent is extended or adjusted under 35 U.S.C. 154(b) by 139 days.

(21) Appl. No.: 15/279,820

(22) Filed: Sep. 29, 2016

(65) Prior Publication Data

US 2018/0088669 A1    Mar. 29, 2018

(51) Int. Cl.
   *G06F 3/01*   (2006.01)
   *A61B 5/00*   (2006.01)
   (Continued)

(52) U.S. Cl.
   CPC ............ *G06F 3/015* (2013.01); *A61B 5/4094* (2013.01); *G06K 9/00744* (2013.01);
   (Continued)

(58) Field of Classification Search
   CPC ....... G06F 3/011; G06F 3/015; A61B 5/4094; A61B 5/0476
   See application file for complete search history.

(56) References Cited

U.S. PATENT DOCUMENTS 5,995,868 A    11/1999  Dorfmeister et al.
6,488,617 B1   12/2002  Katz
(Continued)

FOREIGN PATENT DOCUMENTS

WO    2012102974     8/2012
WO    WO 2015030797 A1 *  3/2015    ........... H04N 13/044

OTHER PUBLICATIONS

International Searching Authority, "International Search Report," issued in connection with international application No. PCT/US2017/046240, dated Nov. 22, 2017, 3 pages.
(Continued)

*Primary Examiner* — Patrick F Marinelli
(74) *Attorney, Agent, or Firm* — Hanley, Flight and Zimmerman, LLC

(57) ABSTRACT

Methods and apparatus for identifying potentially seizure-inducing virtual reality content are disclosed herein. An example apparatus includes a virtual reality presentation device to display virtual reality content for exposure to a user and a neurological data collector to access first neurological response data collected from the user during exposure to the virtual reality content. The example apparatus includes a predictor to generate a prediction on a likelihood that a portion of the virtual reality content will trigger a seizure based on a first vector characterizing the portion and the first neurological response data. The example apparatus includes a content modifier to modify the portion of the virtual reality content into modified virtual reality content in response to the prediction. The content modifier is to transmit the modified virtual reality content to the virtual reality presentation device.

20 Claims, 6 Drawing Sheets

(51) Int. Cl.
*G06T 11/60* (2006.01)
*G06K 9/00* (2006.01)
*G06T 5/00* (2006.01)

(52) U.S. Cl.
CPC .............. *G06T 5/009* (2013.01); *G06T 11/60* (2013.01); *G06T 2207/20208* (2013.01)

(56) References Cited

U.S. PATENT DOCUMENTS

| | | | |
|---|---|---|---|
| 6,549,804 B1 | 4/2003 | Sorb et al. | |
| 6,792,304 B1 | 9/2004 | Silberstein | |
| 7,136,055 B2 * | 11/2006 | Kamijo | G09G 5/02 345/204 |
| 7,630,757 B2 | 12/2009 | Dorfmeister et al. | |
| 7,697,979 B2 | 4/2010 | Martinerie et al. | |
| 7,885,706 B2 | 2/2011 | Ludvig et al. | |
| 7,892,764 B2 | 2/2011 | Xiong et al. | |
| 8,473,024 B2 | 6/2013 | Causevic et al. | |
| 8,768,020 B2 * | 7/2014 | Ferguson | G06K 9/00718 382/128 |
| 9,392,956 B2 | 7/2016 | Luo et al. | |
| 9,618,749 B2 * | 4/2017 | Deleeuw | H04N 13/044 |
| 9,712,736 B2 * | 7/2017 | Kearns | H04N 5/77 |
| 9,785,453 B2 * | 10/2017 | Murakami | G06F 9/44547 |
| 9,807,445 B2 * | 10/2017 | Mountain | H04N 21/4312 |
| 2004/0092809 A1 | 5/2004 | DeCharms | |
| 2004/0155872 A1 * | 8/2004 | Kamijo | G09G 5/02 345/204 |
| 2006/0111644 A1 | 5/2006 | Guttag et al. | |
| 2007/0273611 A1 * | 11/2007 | Torch | A61B 3/0066 345/8 |
| 2010/0198098 A1 | 8/2010 | Sorb et al. | |
| 2012/0022391 A1 | 1/2012 | Leuthardt | |
| 2012/0182206 A1 | 7/2012 | Cok et al. | |
| 2012/0197092 A1 | 8/2012 | Luo et al. | |
| 2012/0215518 A1 * | 8/2012 | Murakami | G06F 9/44547 703/27 |
| 2013/0169880 A1 * | 7/2013 | Ferguson | G06K 9/00718 348/607 |
| 2014/0126877 A1 | 5/2014 | Crawford et al. | |
| 2014/0316191 A1 | 10/2014 | de Zambotti et al. | |
| 2014/0316192 A1 | 10/2014 | de Zambotti et al. | |
| 2016/0026253 A1 * | 1/2016 | Bradski | G02B 27/225 345/8 |
| 2016/0178904 A1 * | 6/2016 | Deleeuw | H04N 13/044 345/8 |
| 2017/0171441 A1 * | 6/2017 | Kearns | H04N 5/77 |
| 2017/0311012 A1 * | 10/2017 | Griffiths | H04N 21/234345 |
| 2017/0323485 A1 * | 11/2017 | Samec | G06T 19/006 |
| 2017/0354341 A1 * | 12/2017 | Kadambi | A61B 5/0476 |
| 2017/0365101 A1 * | 12/2017 | Samec | G02B 27/017 |
| 2018/0088669 A1 * | 3/2018 | Ramaprakash | G06F 3/015 |

OTHER PUBLICATIONS

International Searching Authority, "Written Opinion," issued in connection with international application No. PCT/US2017/046240, dated Nov. 22, 2017, 7 pages.

\* cited by examiner

METHODS AND APPARATUS FOR IDENTIFYING POTENTIALLY SEIZURE-INDUCING VIRTUAL REALITY CONTENT

FIELD OF THE DISCLOSURE

This disclosure relates generally to virtual reality, and, more particularly, to methods and apparatus for identifying potentially seizure-inducing virtual reality content.

BACKGROUND

Photosensitive epilepsy is a type of epilepsy in which seizures are triggered in an individual by visual stimuli that form patterns in time and space, such as flashing lights or contrasting color patterns. A stimulus such as a virtual reality environment may include features that can induce a seizure in an individual with photosensitive epilepsy who is interacting with the virtual reality environment.

BRIEF DESCRIPTION OF THE DRAWINGS

The figures are not to scale. Instead, to clarify multiple layers and regions, the thickness of the layers may be enlarged in the drawings. Wherever possible, the same reference numbers will be used throughout the drawing(s) and accompanying written description to refer to the same or like parts.

DETAILED DESCRIPTION

Figure 1:
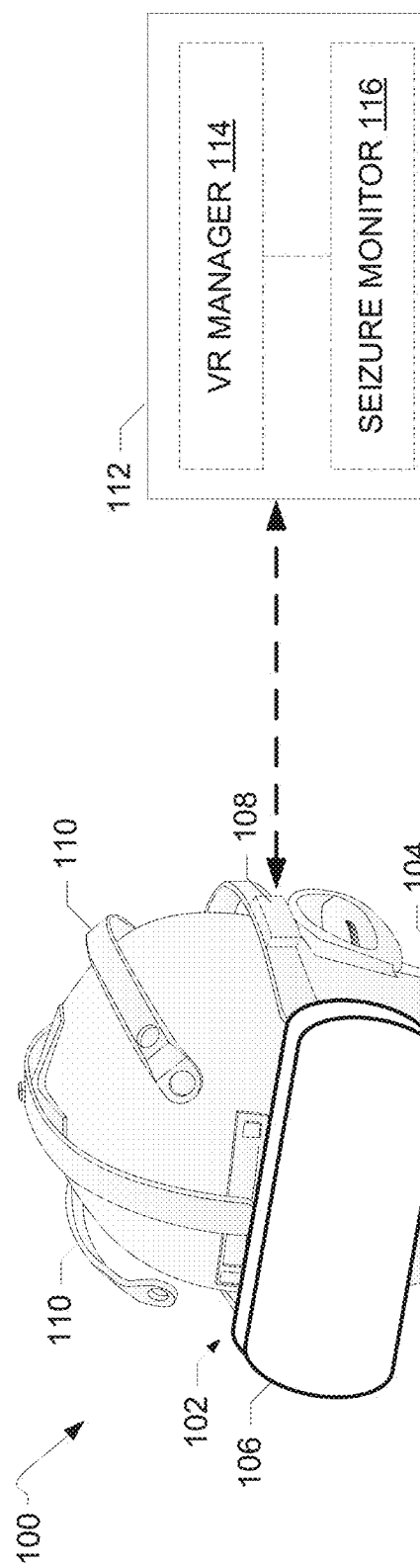
FIG. 1 illustrates an example system including a virtual reality head-mounted device and a processing unit for identifying potentially seizure inducing virtual reality content constructed in accordance with the teachings disclosed herein.

Photosensitive epilepsy is a type of epilepsy in which seizures are triggered in an individual by patterns formed by visual stimuli. Examples of visual stimuli that can trigger a seizure include flashing lights, bright and/or contrasting color patterns (e.g., white bars formed against a black background), flashing white light followed by darkness, and/or color patterns such as red and blue. In some examples, audio stimuli presented with the visual stimuli (e.g., background music) contribute to the triggering of the seizures.

A virtual reality (VR) environment is a digital representation of an environment (e.g., a real or imagery environment) that simulates a user's presence in the environment such that the user can interact with the virtual reality environment. The VR environment can be displayed in any number of ways, for example, via a computer monitor, a virtual reality headset, or another head-mounted device. When the user wears the virtual reality head-mounted device ("VR HMD"), the user can be immersed in the VR environment such that the VR environment substantially occludes and/or replaces the physical environment in the user's perception.

VR environments can include visual stimuli (e.g., flashing lights) that can trigger a photosensitive epilepsy seizure ("PSE seizure") in some users. A PSE seizure that occurs while a user is immersed in a VR environment can result in danger to the user aside from the PSE seizure itself. For example, if the user is wearing a VR HMD, the user may not be able to visualize or accurately perceive his physical surroundings. During a PSE seizure, the user may become disoriented with respect to his physical surroundings, fall, and/or hit one or more objects in the physical environment, which can result in harm to the user. Although a manufacturer of a VR environment and/or a VR HMD may provide warnings to the user that the VR environment can trigger PSE seizures in certain individuals (e.g., via a screen displayed before the VR environment is presented), such warnings do not determine if the user is having a PSE seizure and do not address the PSE seizure triggers in the VR environment. Instead, the user is left to police his own exposure with no technical assistance.

Example systems and methods disclosed herein analyze visual content and/or audio content of a VR environment and neurological response data collected from a user while the user is exposed to the VR environment via, for example, a VR HMD. Based on the analysis of the video and/or audio content and the neurological response data, the examples disclosed herein identify potential PSE seizure triggers in the VR environment and predict whether or not the user is likely to experience a PSE seizure or other negative neurological and/or physiological event while the user is exposed to the VR environment. Some such examples automatically modify one or more visual and/or audio parameters of the VR environment to reduce a likelihood of (e.g., prevent) an occurrence of a PSE seizure as the user interacts with the VR environment.

Disclosed examples monitor a user's neurological activity while the user is interacting with the VR environment. In some examples, electroencephalogram (EEG) sensors are integrated into a VR HMD. The EEG sensors record electrical activity of the user's brain. The resulting EEG signal data is analyzed to identify neurological sensitivities to the VR environment and/or abnormalities in the user's brain activity that may be indicative of an impending PSE seizure or an in-progress PSE seizure.

Disclosed examples also monitor visual and/or audio content of the VR environment with respect to PSE seizure triggering parameters. In some examples, visual parameters such as luminance or hue and/or audio parameters such as a decibel level and/or pattern(s) in a frequency spectrum of an audio stream are identified in the VR environment content. The visual and/or audio parameters are analyzed relative to known and/or learned seizure triggers. Variations in luminance, flashing lights, and/or certain color patterns in visual content are examples of visual seizure triggers.

Based on the neurological signal data measured from the user and the monitoring of the VR environment content, the examples disclosed herein predict whether content of the VR environment is likely to trigger a PSE seizure in the user before the content is presented to the user. Some such examples also determine one or more modifications to the VR environment content to prevent or reduce a likelihood of an occurrence of a PSE seizure. Some such examples modify the content before the content is rendered (e.g., displayed via a screen or output via speakers) to the user. In some examples, an alert is provided to the user advising the user to stop the presentation of the VR environment content and/or to remove the VR HMD to reduce the risk of a PSE seizure. Some disclosed examples predictively modify the VR environment content and/or warn the user of potential seizure triggering content to reduce a likelihood of (e.g., prevent) an occurrence of a PSE seizure in the user while the user is immersed in the VR environment.

In some examples, an onset of a PSE seizure is detected (or attempted to be detected) while the user is viewing the VR environment monitoring neurological data. In some such examples, presentation of the VR environment content is automatically stopped when such an onset is detected. In some such examples, alerts are generated and transmitted (e.g., via text message) to one or more individuals designated by the user informing the individual(s) that the user is experiencing a change in neurological data indicative of a PSE seizure. Thus, disclosed examples may provide for corrective and/or assistive actions based on the user's neurological reaction to the VR environment.

FIG. 1 illustrates an example system 100 constructed in accordance with the teachings of this disclosure for predicting seizures (e.g., a photosensitive epilepsy seizure) in a user interacting with a virtual reality (VR) environment. The example system 100 includes a virtual reality head-mounted device (VR HMD) 102 to be worn by a user 104. The VR HMD 102 includes a virtual reality viewer (VR viewer) 106 and one or more speakers 108. The VR viewer 106 is located over the user's eyes like a mask and displays video content. The speaker(s) 108 are positioned adjacent to and/or covering the ears of the user 104 and provide audio content, which, in some examples, is synchronized with the video content.

The VR HMD 102 also includes a plurality of neurological data collection sensors 110 coupled to the VR HMD 102. In the example of FIG. 1, the sensors 110 of the VR HMD 102 are electroencephalography (EEG) sensors that include one or more electrodes to record electrical activity of the brain of the user 104. However, the VR HMD 102 can include other number(s) and/or type(s) of sensors 110 to collect neurological and/or physiological data from the user 104, such as electrooculography (EOG) sensors, galvanic skin response sensors, and/or electrocardiography (EKG) sensors. As illustrated in FIG. 1, the VR HMD 102 is worn by the user 104 such that the VR viewer 106 covers the eyes of the user 104 and the sensors 110 are disposed about the head of the user 104.

The example system 100 of FIG. 1 includes a processing unit 112 communicatively coupled to the VR HMD 102. The processing unit 112 includes a virtual reality (VR) manager 114 and a seizure monitor 116. The VR manager 114 provides virtual reality content (VR content) for presentation to the user 104 via the VR HMD 102. In the example system 100, the user 104 views visual content of the VR content via the VR viewer 106 of the VR HMD 102. In some examples, the VR content includes audio that is presented to the user 104 via the speaker(s) 108 of the VR HMD 102. The seizure monitor 116 of the illustrated example monitors the VR content and/or the user's reaction to the VR content to determine if a seizure and/or other negative neurological and/or physiological event are likely to be and/or are being induced by the VR content.

In some examples, the processing unit 112 is coupled to the VR HMD 102 such that the processing unit 112 is disposed on the VR HMD 102. For example, in some instances, the VR HMD 102 can receive a mobile device (e.g., a smartphone) such that a display of the mobile device serves as the VR viewer 106. In such examples, the processing unit 112 may be implemented by the processor of the mobile device. In other examples, the processing unit 112 is integral to the VR HMD 102 (e.g., is a dedicated processor mounted to or with the VR viewer 106, the speaker(s) 108, the sensors 110, or another part of the VR HMD 102).

The processing unit 112 of FIG. 1 can be implemented by one or more other devices capable of presenting VR content (e.g., a personal computer) and/or capable of collecting and processing neurological data (e.g., a device that collects neurological data separate from a device presenting the VR content). In some examples, the processing unit 112 is not disposed on the VR HMD 102. Rather, the processing unit 112 is separate from the VR HMD 102 and can be located, for example, in a room where the user 104 is viewing the VR content (e.g., in a gaming console such as an Xbox™, Playstation™, or the like) or worn by the user 104 at a location on the user other than about the head of the user 104 (e.g., on a vest worn by the user 104, on a wrist of the user 104, etc.). In some such examples, the processing unit 112 is communicatively coupled to the VR HMD 102 via, for example, a cable extending between the VR HMD 102 and the processing unit 112. In other examples, the VR HMD 102 and the processing unit 112 are wirelessly coupled such that data is wireless transmitted between the VR HMD 102 and the processing unit 112 (e.g., via Wi-Fi or Bluetooth connections). In some examples, the location of the processing unit 112 (e.g., disposed on the VR HMD 102 or separate from the VR HMD 102) is based on, for example, power required to operate the system 100. A processing unit 112 that requires for higher wattage (e.g., to support higher performance) may be located separate from the VR HMD 102.

In the example system 100) of FIG. 1, the seizure monitor 116 serves to process the data obtained by the sensors 110 to determine if a seizure such as a photosensitive epilepsy seizure is imminent. In the example system 100, the sensors 110 of the VR HMD 102 collect neurological data from the user 104 as the user 104 is exposed to the VR content via the VR viewer 106 and/or the speaker(s) 108. The seizure monitor 116 receives and processes the neurological data collected by the sensors 110. The seizure monitor 116 can perform one or more operations on the neurological data such as filtering the raw signal data, removing noise from the signal data, converting the signal data from analog data to digital data, and/or analyzing the data.

In some examples, the seizure monitor 116 determines that the neurological data collected from the user 104 by the sensors 110 as the user 104 is exposed to the VR content generated by the VR manager 114 is indicative of one or more characteristics of an impending seizure (e.g., a PSE seizure) or an in-progress seizure (e.g., a PSE seizure). In some such examples, the seizure monitor 116 predicts that continued exposure to the VR content may induce a PSE seizure in the user 104 or continue or worsen the PSE seizure symptoms of the user 104. In such examples, the seizure monitor 116 cooperates with the VR manager 114 to modify one or more visual and/or audio parameters of at least a portion of the VR content that has not yet been presented to the user 104. The VR manager 114 transmits the modified VR content for presentation to the user 104 via the VR viewer 106 and/or the speaker(s) 108 of the VR HMD 102. In other examples, the VR manager 114 stops transmission of the VR content to the VR HMD 102 in response to the seizure monitor 116 detecting more than a threshold likelihood that the VR content is likely to induce a seizure or other negative neurological and/or physiological event in the user.

Figure 2:
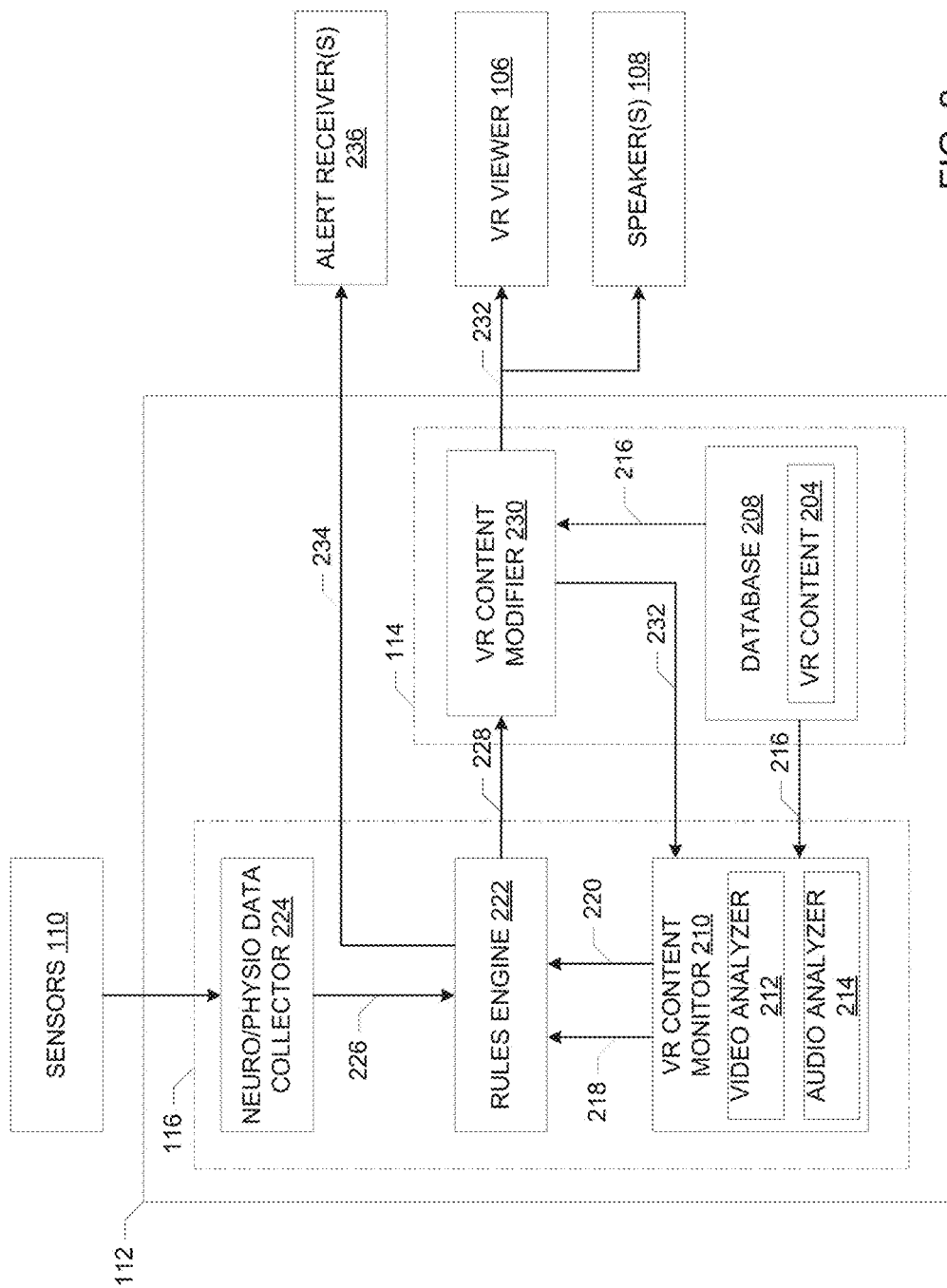
FIG. 2 is a block diagram of an example implementation of the seizure monitor and the virtual reality manager of FIG. 1.

FIG. 2 is a block diagram of an example implementation of the example VR manager 114 and the example seizure monitor 116 of FIG. 1. As mentioned above, the example seizure monitor 116 is constructed to attempt to predict seizures (e.g., photosensitive epilepsy seizures) in a user interacting with a VR environment. The VR manager 114 is constructed to respond to predictions of the seizure monitor 116 by terminating and/or modifying VR content to reduce and/or eliminate visual and/or audio triggers based on the predictions.

The example VR manager 114 of FIG. 2 controls presentation of VR content 204 to a user (e.g., the user 104 of FIG. 1). The VR content 204 is presented to the user via the VR viewer 106 and/or the speaker(s) 108 communicatively coupled to the VR manager 114.

In the example of FIG. 2, the VR content 204 is stored in a database 208 accessed by the VR manager 114. The VR content 204 includes video content including a plurality of video frames. Each frame of the video content includes one or more visual (e.g., video) parameters. An example frame of the VR content 204 can include a visual pattern including two or more colors. In some examples, the VR content 204 includes audio content including one or more audio parameters. A video frame may be synchronized with and/or otherwise associated with an audio stream to be played when the user views the video frame. The respective frames of the video content can be presented, for example, sequentially to the user via the VR viewer 106. In some examples, the VR content 204 includes special effects, such as user hand gestures, that are generated as the user interacts with the VR content 204 in real-time. The audio content is presented to the user via speaker(s) 108.

The video frames and corresponding audio of the VR content 204 are scanned by a virtual reality content monitor (VR content monitor) 210 of the seizure monitor 116 during and/or prior to presentation of the VR content 204 to the user. The VR content monitor 210 of the illustrated example includes a video analyzer 212 and an audio analyzer 214. The video analyzer 212 of the VR content monitor 210 scans the video frames of the VR content 204 for the visual parameters. The audio analyzer 214 of the illustrated example scans the audio for the audio parameters of each corresponding video frame. In some examples, the VR content monitor 210 substantially continuously scans the video frames and corresponding audio of the VR content 204 during operation of the VR HMD 102.

In digital media, content is often broken into a video stream and an audio stream. The video and audio streams are synchronized. The video stream is a sequence of video frames. Although the video stream and the audio stream are often separate, for ease of reference, they are collectively referred to herein as a virtual reality content stream (VR content stream) 216. In some examples, the VR content stream 216 is analyzed as it is presented to the user via the VR viewer 106 and/or the speaker(s) 108. In other examples, the VR content stream 216 is analyzed before it is presented to the user.

The video analyzer 212 of the VR content monitor 210 scans the video frames of the video portion of the VR content stream 216 with respect to the visual parameters of the frames, such as hue, saturation, and value (HSV) and/or luminance (e.g., brightness) of the frames. The video analyzer 212 generates one or more video vectors 218 for the visual parameter(s) of the frames of the VR content stream 216. For example, the video analyzer 212 can detect the red-green-blue (RGB) values of the pixels of a video frame of the VR content stream 216. The video analyzer 212 generates a first video vector 218 indicative of the HSV of the frame based on the RGB values using any of the various past, present, or future algorithms for determining HSV of an image from RGB values. The video analyzer 212 of the illustrated example generates a second video vector 218 indicative the luminance (e.g., brightness) of the frame based on the RGB values of the pixels of the frame. The video stream of the VR content stream 216 is a series of sequential frames (e.g., MPEG frames). The video analyzer 212 of this example analyzes every frame in the sequence. In other examples, the video analyzer 212 analyzes a subset of the frames. The frame(s) undergoing analysis may be selected in any manner (e.g., ever third frame, only iframes, only frames exhibiting a certain characteristic (e.g., a change in DC value, a macroblock characteristic, a slice characteristic, etc.)).

The audio analyzer 214 of the VR content monitor 210 identifies one or more audio parameters of audio of the VR content stream 216, for example, an audio stream to be played during a corresponding video frame. The audio parameters can include decibel values, audio gain (e.g., loudness), or audio levels (e.g., audio signal strength). The audio analyzer 214 generates one or more audio vectors 220 corresponding to the audio parameters. For example, the audio analyzer 214 of the illustrated example maps digital values (e.g., bits) corresponding to the audio parameters of the audio portion of the VR content stream 216 to decibel values.

The VR content monitor 210 of the illustrated example transmits the video vector(s) 218 and the audio vector(s) 220 to a rules engine 222 of the seizure monitor 116. The rules engine 222 analyzes the video vector(s) 218 and/or the audio vector(s) 220 to determine whether the visual and/or audio parameter(s) of the VR content stream 216 correspond to known and/or learned seizure trigger(s). In analyzing the video vector(s) 218 and the audio vector(s) 220, the rules engine 222 of the illustrated example implements a machine learning algorithm that also considers other variables such as neurological data received from the user while viewing the VR content 204 (e.g., while viewing a video frame and/or prior video frames of the VR content 204 and/or associated therewith), user profile data such as age and gender of the user, previously analyzed VR content and/or neurological data (e.g., calibration data), and known and/or learned seizure triggers, as will be disclosed below.

The seizure monitor 116 of FIG. 2 includes a neurological and/or physiological data collector 224. The neurological/physiological data collector 224 of this example communicates with the sensors 110 of the VR HMD 102 of FIG. 1. As the VR content stream 216 is presented to the user via the VR viewer 106 and/or the speaker(s) 108, the neurological/physiological data collector 224 collects neurological and/or physiological data 226 from the user in substantially real-time. For example, the neurological/physiological data collector 224 of this example records electrical activity of the brain of the user detected by the sensors 110 via electrodes to generate brain signal data (e.g., EEG data). In some examples, the neurological/physiological data collector 224 substantially continuously collects and processes data from the sensors 110 into neurological/physiological data 226 during presentation of the VR content stream 216.

The neurological/physiological data collector 224 converts the raw data collected by the sensors 110 into the neurological/physiological data 226 using any of various techniques. For example, the neurological/physiological data collector 224 of the illustrated example filters the neurological/physiological data 226, amplifies the neurological/physiological data 226, and/or removes noise from the neurological/physiological data 226. In other examples, the neurological/physiological data 226 is processed by the rules engine 222. In the illustrated example, the neurological/physiological data collector 224 transmits the neurological/physiological data 226 to the rules engine 222 of the seizure monitor 116. The neurological/physiological data collector 224 may transmit the neurological/physiological data 226 to the rules engine 222 via a wired or wireless connection.

The rules engine 222 of the illustrated example analyzes the video vector(s) 218, the audio vector(s) 220, and the neurological/physiological data 226 relative to known and/or learned seizure triggers and/or calibration data to predict whether the VR content stream 216 is likely to induce a seizure (e.g., a PSE seizure) in the user. If the rules engine 222 predicts that the VR content stream 216 is likely to induce a seizure, the rules engine 222 of the illustrate example determines one or more modifications to the visual and/or audio parameters of the VR content stream 216 to reduce a likelihood of an occurrence of the seizure. In particular, the rules engine 222 of this example generates one or more instructions 228 to modify the VR content stream 216. The rules engine 222 transmits the instruction(s) 228 to a virtual reality content modifier (VR content modifier) 230 of the VR manager 114. The communication between the VR manager 114 and the seizure monitor 116 (and/or any other components in communication with the VR manager 114 and/or the seizure monitor 116, such as the sensors 110) can occur via wired or wireless communication. In some examples, the seizure monitor 116 includes the VR content modifier 230.

Based on the instruction(s) 228 received from the rules engine 222, the VR content modifier 230 modifies one or more video frames and/or audio of the VR content stream 216 to generate a modified VR content stream 232. For example, the rules engine 222 may transmit an instruction 228 directing the VR content modifier 230 to reduce a luminance (e.g., brightness) of one or more video frames of the VR content stream 216 before the frame(s) are presented to the user. Based on the instruction 228, the VR content modifier 230 may modify the frame(s) of the VR content stream 216 (e.g., the RBG values) to reduce the luminance. Thus, the modified VR content stream 232 (or a portion of the modified VR content stream 232) has a reduced luminance relative to the VR content stream 216 prior to modification.

As another example, based on the instruction(s) 228 from the rules engine 222, the VR content modifier 230 may modify a hue value and/or a saturation value of one or more frames of the VR content stream 216 to reduce an intensity of a color pattern presented to the user. Thus, the modified VR content stream 232 includes frame(s) including a color pattern having an adjusted hue value and/or an adjusted saturation value relative to the VR content stream 216 prior to modification. The VR content modifier 230 transmits the modified VR content stream 232 to the VR viewer 106 and/or the speaker(s) 108 for presentation to the user. In examples where the VR content stream 216 has not yet been presented to the user, the modified VR content stream 232 replaces the VR content stream 216. Otherwise, the modification(s) are applied to future portion(s) of the VR content stream 216.

The example VR manager 114 provides feedback to the rules engine 222 with respect to the modified VR content stream 232. As illustrated in FIG. 2, in addition to transmitting the modified VR content stream 232 to the VR viewer 106 and/or the speaker(s) 108, the VR content modifier 230 sends the modified VR content stream 232 to the VR content monitor 210 of the seizure monitor 116. The VR content monitor 210 identifies the visual and/or the audio parameters of the modified VR content stream 232 and transmits the associated video vector(s) 218 and/or audio vector(s) 220 to the rules engine 222. Also, as the user views the modified VR content stream 232, the neurological/physiological data collector 224 collects and/or develops the neurological/physiological data 226 from the user in substantially real-time and transmits the neurological/physiological data 226 to the rules engine 222. The rules engine 222 analyzes the video and/or audio vector(s) 218, 220 for the modified VR content stream 232 and the corresponding neurological/physiological data 226 collected from the user. The rules engine 222 determines whether further modification(s) to the modified VR content stream 232 are required to substantially prevent a seizure (e.g., a PSE seizure) or other negative neurological and/or physiological event. If further modification(s) are appropriate, the rules engine 222 of the illustrated example generates one or more instructions 228 to affect further modification of the modified VR content stream 232 by the VR content modifier 230.

In some examples, the rules engine 222 determines that the VR content stream 216 is not likely to induce a seizure or other negative neurological and/or physiological event based on the neurological/physiological data 226, the video vector(s) 218, and/or the audio vector(s) 220. In such examples, the rules engine 222 determines that modification of the VR content stream 216 is not required. The rules engine 222 sends an instruction 228 to the VR content modifier 230 to transmit the VR content stream 216 to the VR viewer 106 and/or the speaker(s) 108. In such examples, the modified VR content stream 232 shown in FIG. 2 as transmitted or output to the VR viewer 106 and/or the speaker(s) 108 for presentation to the user is not actually changed, but instead is the same or substantially the same as the unmodified VR content stream 216.

In other examples, the rules engine 222 determines that the user is or is likely experiencing a seizure (e.g., a PSE seizure) or other negative neurological and/or physiological event based on the neurological/physiological data 226 collected during exposure of the user to the VR content stream 216, the modified VR content stream 232, and/or other content presented before the presentation of the VR content stream 216 or the modified VR content stream 232. For example, if the rules engine 222 detects that the neurological/physiological data 226 collected during exposure of the user to the modified VR content stream 232 includes patterns indicative of a seizure (e.g., a PSE seizure) or an impending seizure (e.g., a PSE seizure), the rules engine 222 sends an instruction 228 to the VR content modifier 230 to stop transmission of the VR content to the VR viewer 106 and/or the speaker(s) 108. Thus, the example processing unit 112 dynamically responds to the user's neurological experience while the user is exposed to the VR content 204.

In some examples, the rules engine 222 generates one or more alerts 234 based on the analysis of the neurological/physiological data 226, the video vector(s) 218, and/or the audio vector(s) 220 while the user is exposed to the VR content stream 216 or the modified VR content stream 232. The alert(s) 234 are transmitted to one or more alert receivers 236. The alert(s) 234 can include a visual warning and/or an audio warning to the user recommending that the user stop the presentation of the VR content 204 (e.g., by turning off the VR HMD 102). In such examples, the alert(s) 234 are transmitted to the VR viewer 106 and/or the speaker(s) 108 for presentation to the user. Thus, in some examples, the VR HMD 102 is the alert receiver 236.

In some examples, the rules engine 222 may additionally or alternatively transmit one or more alert(s) 234 in the form of a message (e.g., a text message) to a third party designated by the user of the VR HMD 102. In such examples, the alert receiver 236 can be implemented by, for example, a mobile device owned or leased by the third party. For example, the rules engine 222 may transmit the alert(s) 234 to the mobile device of the third party if the neurological/physiological data 226 indicates that the user of the VR HMD 102 may be experiencing a seizure (e.g., a PSE seizure) or other negative neurological and/or physiological event. Thus, the example processing unit 112 of the illustrated example notifies the third party that the user may need medical attention.

As discussed above, the example processing unit 112 monitors the VR content 204 and/or the user's neurological response to the VR content 204. Based on the monitoring, the example processing unit 112 predicts whether the VR content 204 is likely to induce a seizure (e.g., a PSE seizure) in the user. The example processing unit 112 dynamically adjusts or modifies the frame with respect to seizure triggers. Further, the example processing unit 112 of FIG. 2 generates feedback with respect to the user's neurological response to the modified VR content stream 232 and, thus, provides for continued monitoring and corrective action to address the potential for seizures (e.g., PSE seizures).

Figure 3:
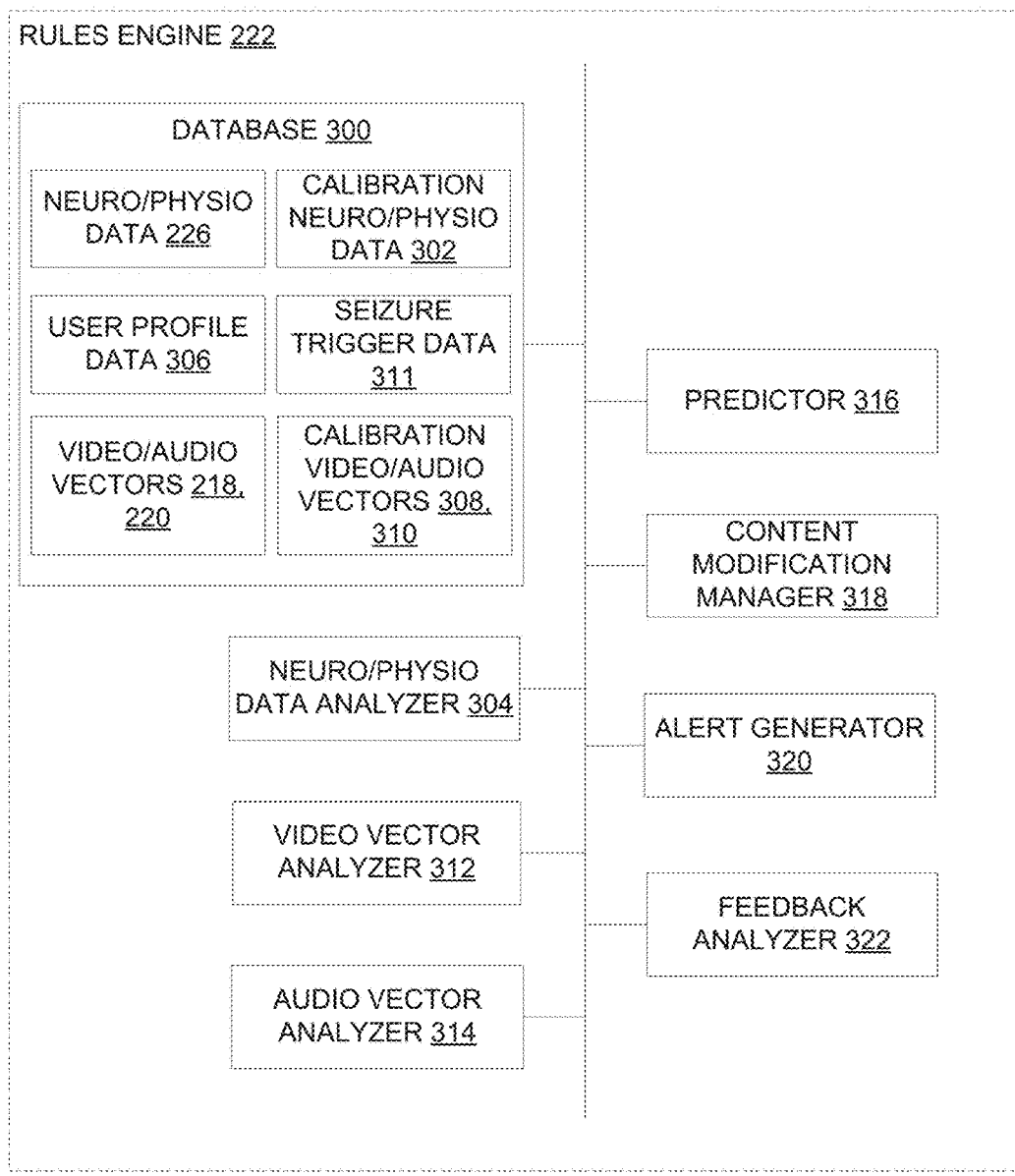
FIG. 3 is a block diagram of an example implementation of the rules engine of FIG. 2.

FIG. 3 is a block diagram of an example implementation of the example rules engine 222 of FIG. 2. The rules engine 222 of the example of FIG. 3 includes a database 300. In some examples, the database 300 is implemented by the database 208 of the VR manager 114 of FIG. 2. As disclosed above, the neurological/physiological data collector 224 of the example processing unit 112 of FIG. 2 transmits the neurological/physiological data 226 collected from the user while the user is exposed to the VR content 204 (including, e.g., the example VR content stream 216) to the rules engine 222. The database 300 stores the neurological/physiological data 226 received from the neurological/physiological data collector 224.

The database 300 of the rules engine 222 also stores calibration neurological/physiological data 302. The calibration neurological/physiological data 302 includes neurological data previously collected from one or more users exposed to the VR content 204 or different VR content. The calibration neurological/physiological data 302 includes neurological data collected during a seizure (e.g., a PSE seizure) experienced by one or more users exposed to the VR content 204 and/or different VR content.

In some examples, the calibration neurological/physiological data 302 is collected from the same user to whom the VR content 204 is presented via the VR viewer 106 and/or the speaker(s) 108 of FIG. 2. For example, the user 104 of the VR HMD 102 of FIG. 1 can be shown VR content different from the VR content 204 of FIG. 2 to collect baseline neurological data from the user 104 before the user 104 is exposed to the VR content 204. The baseline neurological data can be used by the rules engine 222 to identify changes in the neurological/physiological data 226 while the user is exposed to the VR content 204. In some examples, the calibration neurological/physiological data 302 includes neurological and/or physiological data known to induce a seizure (e.g., a PSE seizure) and/or other negative neurological/physiological response.

The rules engine 222 of the illustrated example includes a neurological/physiological data analyzer 304. The neurological/physiological data analyzer 304 analyzes the neurological/physiological data 226 received from the neurological/physiological data collector 224 of FIG. 2 while the user is exposed to the VR content 204 to identify patterns in the neurological/physiological data 226 indicative of an onset of a seizure (e.g., a PSE seizure), an in-progress seizure (e.g., a PSE seizure), and/or other negative neurological and/or physiological event. For example, the neurological/physiological data analyzer 304 analyzes the neurological/physiological data 226 collected from the user during presentation of the VR content stream 216.

The neurological/physiological data analyzer 304 detects changes in the neurological/physiological data 226 over time, such as amplitude and/or frequency changes in the signal data. For example, spike, polyspikes, and/or spike-and-wave complexes in EEG data are known to be associated with a user experiencing a PSE seizure. The neurological/physiological data analyzer 304 recognizes such characteristics or features in the neurological/physiological data 226 (e.g., EEG data). The neurological/physiological data 226 can be analyzed based on predefined time intervals such as time intervals having a duration of 1-2 seconds. For example, the neurological/physiological data analyzer 304 can detect an onset of a seizure (e.g., a PSE seizure) while the user 104 is exposed to the VR content stream 216 based on changes in the neurological/physiological data 226 occurring within a 1-2 second time interval, such as a sudden increase in the presence of spikes in the signal data. If the increased presence of spikes in the signal data is maintained or if the frequency and/or amplitude of the spikes increases for a predetermined amount of time, such as 3 seconds from the detection of the onset of the signal data changes, the neurological/physiological data analyzer 304 determines that the user 104 may be experiencing a seizure (e.g., a PSE seizure).

In some examples, the neurological/physiological data analyzer 304 compares the neurological/physiological data 226 collected while the user is exposed to the example VR content stream 216 to the calibration neurological/physiological data 302. For example, the neurological/physiological data analyzer 304 compares pattern(s) detected in the neurological/physiological data 226 to patterns in brain signal data collected during a seizure (e.g., a PSE seizure experienced by the user 104 of the VR HMD 102 or other users) to identify similarities between the data. In some examples, the neurological/physiological data analyzer 304 compares the neurological/physiological data 226 to the calibration neurological/physiological data 302 collected from the user (e.g., the user 104) to identify abnormalities in the neurological/physiological data 226 that may be indicative of a seizure (e.g., a PSE seizure).

The database 300 of the rules engine 222 also stores user profile data 306. The user profile data 306 includes data about the user viewing the VR content 204 (e.g., the user 104 of the VR HMD 102 of FIG. 1), such as age and gender. In some examples, the user profile data 306 includes data about the user's medical history, such as whether the user has a history of PSE seizures. The user profile data 306 can be obtained from one or more user inputs received via the processing unit 112 of FIG. 2.

The database 300 of the rules engine 222 also stores the video vector(s) 218 and the audio vector(s) 220 generated by the VR content monitor 210 of the example seizure monitor 116 of FIG. 2 for the VR content 204 (e.g., the VR content stream 216 and/or the modified VR content stream 232). The database 300 also stores calibration video vectors 308 and/or calibration audio vectors 310 corresponding to portions of VR content (e.g., the VR content 204 of FIG. 2 or different VR content) that induced seizures (e.g., PSE seizures) in one or more users. The calibration video vectors 308 and/or the calibration audio vectors 310 correspond to the VR content that was presented when one or more user(s) (e.g., the user 104 of the VR HMD 102 or other users) experienced a seizure as indicated by the calibration neurological/physiological data 302.

The example database 300 stores seizure trigger data 311. The seizure trigger data 311 includes luminance values, saturation values, patterns, colors, audio decibel levels, patterns in an audio frequency spectrum. etc. known to induce seizures (e.g., PSE seizures) in some users. For example, the calibration video and/or audio vectors 308, 310 contain data about visual and/or audio parameters of VR content that previously induced a seizure (e.g., a PSE seizure). Thus, the calibration video and/or audio vectors 308, 310 contain known and/or learned seizure triggers with respect to visual and/or audio parameters of the VR content that can be stored as seizure trigger data 311. For example, the calibration video vectors 308 include luminance values of one or more video frames that induced seizures (e.g., PSE seizures). The calibration audio vectors 310 include decibel values of audio that may have contributed to inducing seizures (e.g., PSE seizures). In other examples, the seizure trigger data 311 includes known and/or learned seizure triggers from inputs other than the calibration video and/or audio vectors 308, 310 (e.g., user inputs provided to the rules engine 222 based on research and/or third party studies).

The rules engine 222 includes a video vector analyzer 312 and an audio vector analyzer 314. The video vector analyzer 312 analyzes the video vector(s) 218 generated by the VR content monitor 210 of FIG. 2 for the VR content 204. For example, the video vector analyzer 312 attempts to detect a change in luminance values between a first video vector 218 for a given frame (e.g., a MPEG frame) of the VR content stream 216 and a second video vector 218 for an earlier frame of the VR content stream 216 presented prior to the given frame. The change detected by the video vector analyzer 312 can indicate, for example, an increase in brightness between the frames in the VR content stream 216. The video vector analyzer 312 also compares the luminance value for the given frame indicated by a corresponding first video vector 218 to luminance values stored in the seizure trigger data 311.

The audio vector analyzer 314 analyzes the audio vector(s) 220 generated by the VR content monitor 210 for the corresponding ones of the video frames of the VR content stream 216. The audio vector analyzer 314 attempts to determine a decibel level and/or pattern(s) in a frequency spectrum for a portion of the audio stream corresponding to the video frame (e.g., an audio frame) based on the audio vector(s) 220. For example, the audio vector analyzer 314 may detect a change in decibels of an audio stream between a first audio vector 220 for a first portion of the VR content stream 216 and a second audio vector 220 for a second (e.g., later) portion of the VR content stream 216. The change detected by the audio vector analyzer 314 can indicate, for example, an increase in an intensity of the audio stream. The audio vector analyzer 314 also compares the decibel values indicated by first audio vector 220 to values stored in the seizure trigger data 311.

The rules engine 222 of the example of FIG. 3 includes a predictor 316. The predictor 316 predicts whether portions of the VR content 204 under analysis is likely to induce a seizure (e.g., a PSE seizure) and/or other negative neurological/physiological event in the user using the example VR HMD 102 of FIG. 1. The predictor 316 of this example makes the prediction based on the analysis of the neurological/physiological data 226 by the neurological/physiological data analyzer 304, the analysis of the video vector(s) 218 by the video vector analyzer 312, the analysis of the audio vector(s) 220 by the audio vector analyzer 314, and/or the user profile data 306.

The predictor 316 of the illustrated example utilizes a machine learning algorithm to predict whether the VR content stream 216 is likely to induce a seizure (e.g., a PSE seizure) and/or other negative neurological/physiological event) in the user. The learning algorithm can be, for example, a supervised learning algorithm (e.g., neural networks, decision tree learning, etc.). The learning algorithm can be stored in the database 300 of the rules engine 222. The predictor 316 learns from the calibration neurological/physiological data 302 and/or the calibration video and/or audio vectors 308, 310 with respect to VR content that induced seizures (e.g., PSE seizures) in one or more users (including, in some examples, the user 104 of the VR HMD 102 of FIG. 1). Based on the learned data, the predictor 316 determines whether one or more video and/or audio portions of the VR content stream 216 is likely to induce a seizure (e.g., a PSE seizure) in the user.

For example, the predictor 316 analyzes the calibration neurological/physiological data 302 indicative of seizures (e.g., PSE seizures). The predictor 316 identifies the calibration video and/or audio vectors 308, 310 corresponding to the VR content to which the user(s) were exposed when the user(s) experienced the seizures. For example, the predictor 316 identifies the saturation and hue values of the VR content (e.g., video frame(s)) that was visually displayed during the PSE seizures. The predictor 316 also identifies the decibel level and/or patterns in the frequency spectrum of the audio stream that was playing when the user(s) experienced the seizures. Thus, the predictor 316 learns how users respond to VR content having certain visual and/or audio parameters.

The predictor 316 analyzes the neurological/physiological data 226 collected from the user while exposed to the VR content 204, the user profile data 306 for the user, the video and/or audio vectors 218, 220, and/or the seizure trigger data 311 in view of the learned data. Based on the analysis of the data collected for the VR content 204 relative to the learned data, the predictor 316 predicts whether the VR content stream 216 is likely to induce a PSE seizure in the user (e.g., the user 104 of FIG. 1).

The following example is provided for illustrative purposes with respect to the predictive analysis performed by the predictor 316. Based on the analysis of the video vector(s) 218, the video vector analyzer 312 determines that a current sequence of video frames of the VR content stream 216 under analysis includes flashing lights. The video vector analyzer 312 may detect that the previous video frames of the VR content 204 did not include flashing lights and, thus, the current sequence of frames includes a change in visual content relative to the other frames. Also, the neurological/physiological data analyzer 304 identifies a change in amplitude and/or frequency of spikes in the neurological/physiological data 226 collected from the user occurring over a 1 second time interval while the user is exposed to the current sequence of frames. In this example, the user profile data 306 indicates that the user is over age 60 and has previously experienced a PSE seizure. The predictor 316 references the learned data (e.g., the calibration neurological/physiological data 302, the calibration video and/or audio vectors 308, 310, and/or the seizure trigger data 311), which can indicate, for example, that the introduction of flashing lights can induce seizures (e.g., PSE seizures) in some users. In view of the learned data and based on the determination that the current sequence of frames includes flashing lights and that the neurological/physiological data 226 exhibits a pattern indicative of an onset of a seizure in a user over the age of 60 with a history of PSE seizures, the predictor 316 predicts that that the current sequence of frames of the VR content stream 216 under analysis is likely to induce a seizure (e.g., a PSE seizure) in the user. In the foregoing example, the predictor 316 provides for a user-specific prediction of whether the VR content stream 216 is likely to induce a seizure in the user based on the analysis of the user's neurological/physiological data 226 and the user profile data 306 for the user.

If the predictor 316 predicts that the current sequence of video frames of the VR content stream 216 is likely to induce a seizure and/or other negative neurological/physiological event, the predictor 316 flags the VR content stream 216 and/or the portion of the VR content stream 216 including the sequence of video frames as including seizure trigger content. The identification of the VR content stream 216 as including seizure trigger content (e.g., video and/or audio parameters likely to induce a seizure and/or other negative neurological/physiological response in a user) is stored in the database 300. In some examples, the visual and/or audio parameters of the VR content stream 216 and/or the portion(s) of the VR content stream 216 are stored with the identification of the VR content stream 216 as including seizure trigger content in the database 300 (e.g., as the seizure trigger data 311). Thus, the rules engine 222 classifies VR content stream 216 (e.g., the video and/or audio portions). The classification can be used to identify seizure triggers in other VR content having similar visual and/or audio parameters and/or invoking similar neurological/physiological responses in users. The classification can also be used to preemptively warn VD HMD users and/or to preemptively modify the VR content across users. The prediction of the VR content stream 216 as likely to induce a seizure and/or other negative neurological/physiological response in a user and the corresponding visual and/or audio parameters of the VR content stream 216 are also used to update or refine the learning algorithm used by the predictor 316, as will be disclosed below.

The rules engine 222 of this example includes a content modification manager 318. If the predictor 316 identifies the VR content stream 216 as including seizure trigger content, the predictor 316 sends a message to the content modification manager 318. The content modification manager 318 analyzes the video vector(s) 218 and/or the audio vector(s) 220 of the VR content stream 216 to determine one or more modifications to the visual and/or audio parameters of the VR content stream 216. The content modification manager 318 determines a factor (e.g., an amount, a percentage) by which to adjust the visual and/or the audio parameters to reduce the likelihood of an occurrence of a seizure (e.g., a PSE seizure) and/or other negative neurological/physiological event in the user.

For example, the content modification manager 318 of this example determines an amount by which to reduce a saturation value (e.g., an intensity) of one or more colors of the video frame(s) of the VR content stream 216. In some examples, the content modification manager 318 determines the amount by which to reduce the saturation based on the seizure trigger data 311 such that the saturation value is below a saturation value identified as a known trigger. The content modification manager 318 can determine other modifications to the video frame(s), such as reducing or eliminating flashing color patterns, modifying or changing colors, etc. In some examples, the content modification manager 318 determines a modification for one or more parameters of the VR content stream 216 (e.g., a modification to an individual color in the video frame(s)). In other examples, the content modification manager 318 determines a modification to be applied to the VR content stream 216 as a whole (e.g., a modification to all colors in the video frame(s)).

The content modification manager 318 of some examples also determines a factor by which to adjust one or more audio parameters of the VR content stream 216. For example, the content modification manager 318 can determine an amount by which to reduce a decibel level of the audio stream. In some examples, the content modification manager 318 determines that the audio stream should be muted. In some examples, the content modification manager 318 determines the amount by which to reduce the decibel level based on the seizure trigger data 311 such that the decibel level is below a decibel level identified as a known trigger.

The content modification manager 318 generates one or more instructions 228 with respect to the modification(s) of the visual and/or audio parameters. The rules engine 222 transmits the instruction(s) 228 to the VR content modifier 230 of the VR manager 114 of FIG. 2. As disclosed above, the VR content modifier 230 modifies VR content stream 216 to achieve frames exhibiting the desired visual and/or audio parameters based on the instruction(s) 228. The modified VR content stream 232 generated in this fashion is then transmitted to the VR viewer 106 and/or the speaker(s) 108 (e.g., to replace the VR content stream 216 that has not yet been presented).

In some examples, based on the neurological/physiological data 226 received from the user while the user is exposed to the VR content 204 (e.g., the VR content stream 216 or the modified VR content stream 232), the predictor 316 determines that the user is experiencing a seizure (e.g., a PSE seizure). For example, the predictor 316 can determine that the user is experiencing a seizure (e.g., a PSE seizure) based on similarities between the patterns in the neurological/physiological data 226 identified by the neurological/physiological data analyzer 304 and the calibration neurological/physiological data 302 collected during prior seizures (e.g., for the user 104 of the VR HMD 102 of FIG. 1 or other users). In such examples, the content modification manager 318 generates the one or more instructions 228 to stop presentation of the VR content 204.

In some examples, the predictor 316 determines that the VR content stream 216 is not likely to induce a seizure (e.g., a PSE seizure) in the user. For example, if the video vector analyzer 312 does not detect any changes in the video vector(s) 218 for a current sequence of video frames of the VR content stream 216 under analysis relative to vectors for previously presented frames of the VR content 204 and the neurological/physiological data analyzer 304 does not detect any changes in the neurological/physiological data 226 collected from the user during exposure to the VR content 204, the predictor 316 may determine that the VR content stream 216 is not likely to induce a seizure (e.g., a PSE seizure) in the user. In some such examples, the predictor 316 analyzes the neurological/physiological data 226 relative to the calibration neurological/physiological data 302 for the user to determine if the neurological data exhibits any abnormal patterns despite the absence of changes in the visual parameters between the current sequence of frames and the earlier sequence of frames. In examples where the predictor 316 determines that the VR content stream 216 is not likely to induce a seizure in the user, the rules engine 222 instructs the VR content modifier 230 to transmit the VR content stream 216 without modifications to the VR viewer 106 and/or the speaker(s) 108.

The example rules engine 222 also includes an alert generator 320. The alert generator 320 generates the one or more alerts 234 for transmission to the alert receiver(s) 236, as disclosed above in connection with FIG. 2. For example, if the predictor 316 identifies the VR content stream 216 and/or portion(s) of the VR content stream 216 as including seizure trigger content, the predictor 316 sends a message to the alert generator 320 to generate one or more visual and/or audio alerts 234 warning the user (e.g., the user 104 of the VR HMD 102 of FIG. 1) that the VR content 204 may induce a PSE seizure. In some examples, the alert generator 320 automatically references previous classifications of the VR content 204 (or other VR content) stored in the database 300 to determine if the alert(s) 234 should be generated.

In some examples, the alert generator 320 generates the alert(s) 234 for transmission to one or more third parties designated by the user. Contact information for the one or more third parties can be received from one or more user inputs, via, for example the processing unit 112 of FIG. 2. The contact information for the one or more third parties can be stored in the database 300 of the rules engine 222 for reference by the alert generator 320.

The rules engine 222 includes a feedback analyzer 322. As disclosed above with respect to the example processing unit 112 of FIG. 2, the VR content modifier 230 sends the modified VR content stream 232 to the VR content monitor 210 for substantially continuous monitoring of the user's response to the VR content 204 based on the neurological/physiological data 226 collected from the user. The feedback analyzer 322 of the rules engine 222 analyzes the neurological/physiological data 226 collected from the user while the user is exposed to the modified VR content stream 232 and the video and/or audio vectors 218, 220 associated with the modified VR content stream 232.

The neurological/physiological data 226 collected from the user while the user is exposed to the modified VR content stream 232 is used during analysis of one or more upcoming (e.g., not yet presented) streams of the VR content 204. For example, based on the neurological/physiological data 226 collected from the user during exposure to the modified VR content stream 232 and the visual/audio parameters of the upcoming stream(s), the predictor 316 predicts whether or not the upcoming stream(s) are likely to induce a seizure (e.g., a PSE seizure) and/or other negative neurological/physiological event in the user. Thus, the substantially real-time monitoring of the user's neurological/physiological response to the VR content 204 is used to predict the neurological/physiological effect of the upcoming stream(s) on the user and, in some examples, to modify the upcoming VR content stream(s) if the predictor 316 predicts that the upcoming VR content stream(s) are likely to induce a seizure (e.g., a PSE seizure) and/or other negative neurological/physiological event in the user. For example, the predictor 316 and/or the feedback analyzer 322 may determine that the user is still at risk for an impending seizure or is experiencing a seizure based on the analysis of the neurological/physiological data 226 collected during presentation of the modified VR content stream 232. In such examples, the predictor 316 and/or the feedback analyzer 322 communicate with the content modification manager 318 and/or the alert generator 320 to determine corrective actions such as modifying the upcoming VR content stream(s), generating one or more alerts 234, and/or stopping transmission of the VR content 204.

The feedback analyzer 322 determines whether the modifications to the VR content stream 216 (i.e., the modifications that generated the modified VR content stream 232) substantially mitigated the risk of a seizure (e.g., a PSE seizure) and/or other negative neurological/physiological event in the user. For example, if the neurological/physiological data analyzer 304 detects a decrease in an amplitude and/or frequency of spikes in the neurological/physiological data 226 collected from the user while the user is exposed to the modified VR content stream 232 (e.g., relative to the neurological/physiological data 226 collected before presentation of the modified VR content stream 232), the feedback analyzer 322 determines that the modifications to the visual and/or audio parameters of the VR content stream 216 were effective in reducing the risk of a seizure (e.g., a PSE seizure). The feedback analyzer 322 stores the effective modifications in the database 300 for use by the content modification manager 318 with respect to modification of other portions of the VR content 204 and/or different VR content. Thus, the rules engine 222 learns from the feedback to increase accuracy in predicting whether a portion (e.g., the VR content stream 216) of the VR content 204 is likely to induce a seizure (e.g., PSE seizure) and how to effectively mitigate the risk of a seizure with modifications to the VR content 204.

The feedback analyzer 322 also updates or refines the learning algorithm used by the predictor 316. For example, based on the prediction by the predictor 316 that the VR content stream 216 is likely to induce a seizure (e.g., a PSE seizure) and/or other negative neurological/physiological event in the user, the visual and/or audio parameters of the VR content stream 216, and the user's neurological/physiological response to the modified VR content stream 232, the feedback analyzer 322 updates one or more variables or parameters of the learning algorithm. Thus, the rules engine 222 implements a learned model that is refined based on the predictions by the predictor 316 and the user's response to the VR content 204. The refinement of the learning algorithm improves the ability of the rules engine 222 to predict whether or not upcoming VR content 204 (or other VR content) is likely to induce a seizure (e.g., a PSE seizure) and/or other neurological/physiological event in the user (or other users).

Figure 4:
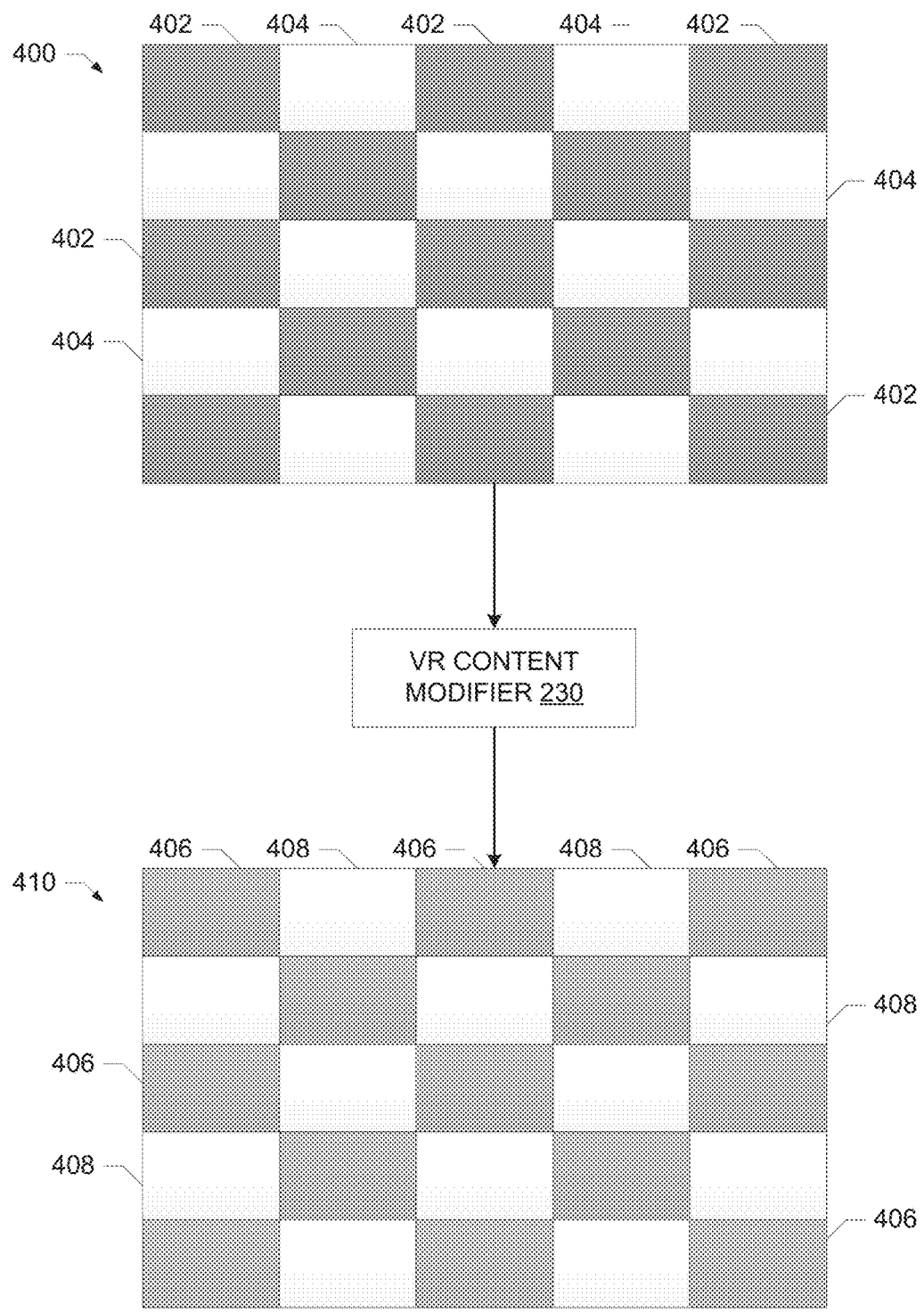
FIG. 4 illustrates example virtual reality content and example modified virtual reality content.

FIG. 4 illustrates an example modification of an example video frame 400 of the VR content 204 of FIG. 2 to generate a modified frame 410 for presentation to the user via the VR viewer 106. The example frame 400 is a part of a sequence of frames of the VR content stream 216. The example frame 400 includes a pattern including a plurality of first squares 402 having first color (e.g., red) and a plurality of second squares 404 having a second color (e.g., blue). As an example, each of the first squares 402 of the frame 400 have a hue value of 0 and a saturation value of 255. Each of the second squares 404 of the frame 400 have a hue value of 170 and a saturation value of 255. In some examples, when the frame 400 is presented as a part of the sequence of frames of the VR content stream 216, the user perceives the pattern of first and second squares 402, 404 as flashing in an alternating sequence.

In some examples, based on the hue and saturation values for the colored pattern of the frame 400 (e.g., as indicated by one or more video vectors 218), the neurological/physiological data 226 collected from the user while exposed to the sequence of frames including the frame 400 (and/or frames presented prior to the sequence of frames including the frame 400), the calibration video vectors 308, and/or the seizure trigger data 311, the rules engine 222 predicts that the sequence of frames including the frame 400 is likely to induce a PSE seizure in the user. The prediction by rules engine 222 that sequence of frames including the frame 400 is likely to induce a PSE seizure can also be based on, for example, the calibration neurological/physiological data 302, the user profile data 306, the calibration video vectors 308, and/or other learned data as disclosed above in connection with FIGS. 2 and 3.

Upon predicting that the sequence of frames including the frame 400 includes visual parameters likely to induce a PSE seizure in the user, the rules engine 222 sends one or more instructions 228 to the VR content modifier 230 to modify the sequence of frames, including the example frame 400. The VR content modifier 230 modifies the example frame 400 to generate the modified frame 410. For example, the VR content modifier 230 adjusts the saturation values of the respective first and second squares 402, 404. As a result of the modification, the modified frame 410 includes modified first squares 406 having a saturation value of 181 and modified second squares 408 having a saturation value of 181. In some examples, the VR content modifier 230 modifies the saturation values for first and second squares 402, 404 differently, only modifies saturation values for one of the first or second squares 402, 404, modifies the hue values of the first and/or second squares 402, 404, etc. The VR content modifier 230 can modify the other frames of the sequence that includes the frame 400 with similar and/or different modifications as applied to the example frame 400. By reducing the saturation values of the first and second squares 402, 406, the VR content modifier 230 reduces the intensity of the pattern of the modified frame 410 relative to the unmodified frame 400 to mitigate the risk of a PSE seizure in the user.

While an example manner of implementing the example processing unit 112, the example VR manger 114, the example seizure monitor 116, and the example rules engine 222 are illustrated in FIGS. 1-3, one or more of the elements, processes and/or devices illustrated in FIGS. 1-3 may be combined, divided, re-arranged, omitted, eliminated and/or implemented in any other way. Further, the example VR HMD 102, the example VR viewer 106 the example processing unit 112, the example VR manager 114, the example seizure monitor 116, the example databases 208, 300, the example VR content monitor 210, the example video analyzer 212, the example audio analyzer 214, the example rules engine 222, the example neurological/physiological data collector 224, the example VR content modifier 230, the example alert receiver(s) 236, the example neurological/physiological data analyzer 304, the example video vector analyzer 312, the example audio vector analyzer 314, the example predictor 316, the example content modification manager 318, the example alert generator 320, the example feedback analyzer 322, and/or, more generally, the example system 100 may be implemented by hardware, software, firmware and/or any combination of hardware, software and/or firmware. Thus, for example, any of the example VR HMD 102, the example VR viewer 106, the example processing unit 112, the example VR manager 114, the example seizure monitor 116, the example databases 208, 300, the example VR content monitor 210, the example video analyzer 212, the example audio analyzer 214, the example rules engine 222, the example neurological/physiological data collector 224, the example VR content modifier 230, the example alert receiver 236, the example neurological/physiological data analyzer 304, the example video vector analyzer 312, the example audio vector analyzer 314, the example predictor 316, the example content modification manager 318, the example alert generator 320, the example feedback analyzer 322, and/or, more generally, the example system 100 could be implemented by one or more analog or digital circuit(s), logic circuits, programmable processor(s), application specific integrated circuit(s) (ASIC(s)), programmable logic device(s) (PLD(s)) and/or field programmable logic device(s) (FPLD(s)). When reading any of the apparatus or system claims of this patent to cover a purely software and/or firmware implementation, at least one of the example, VR HMD 102, the example VR viewer 106, the example processing unit 112, the example VR manager 114, the example seizure monitor 116, the example databases 208, 300, the example VR content monitor 210, the example video analyzer 212, the example audio analyzer 214, the example rules engine 222, the example neurological/physiological data collector 224, the example VR content modifier 230, the example alert receiver 236, the example neurological data analyzer 304, the example video vector analyzer 312, the example audio vector analyzer 314, the example predictor 316, the example content modification manager 318, the example alert generator 320, the example feedback analyzer 322, and/or, more generally, the example system 100 is/are hereby expressly defined to include a tangible computer readable storage device or storage disk such as a memory, a digital versatile disk (DVD), a compact disk (CD), a Blu-ray disk, etc. storing the software and/or firmware. Further still, the example systems 100, 200 of FIGS. 1-3 may include one or more elements, processes and/or devices in addition to, or instead of, those illustrated in FIGS. 1-3, and/or may include more than one of any or all of the illustrated elements, processes and devices.

Figure 5:
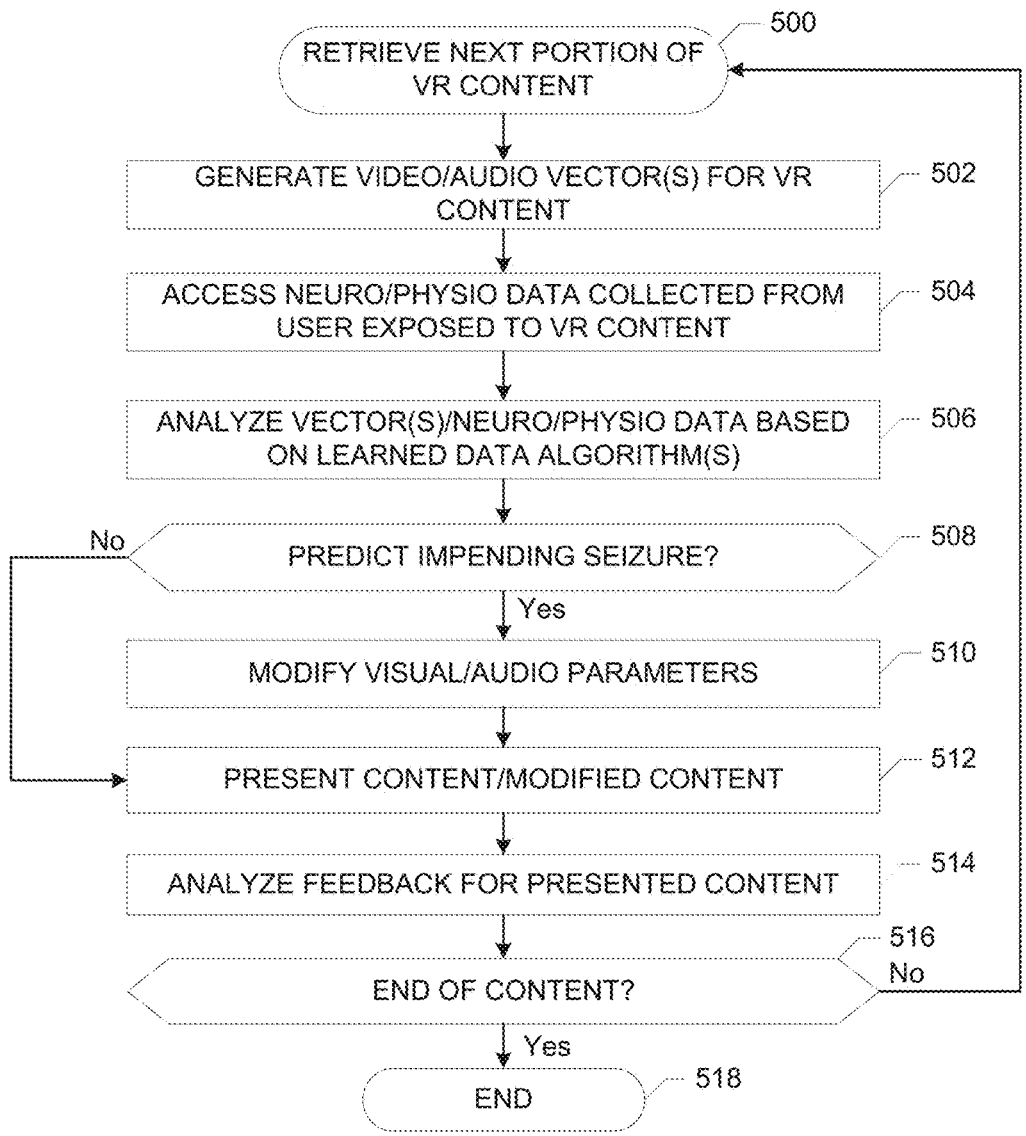
FIG. 5 is a flowchart representative of example machine readable instructions that may be executed to implement the example systems of FIGS. 1-3.

A flowchart representative of example machine readable instructions which may be executed to implement the example system 100 and/or components thereof illustrated in FIG. 1-3 is shown in FIG. 5. In this example, the machine readable instructions comprise a program for execution by a processor such as the processor 612 shown in the example processor platform 600 discussed below in connection with FIG. 6. The program may be embodied in software stored on a tangible computer readable storage medium such as a CD-ROM, a floppy disk, a hard drive, a digital versatile disk (DVD), a Blu-ray disk, or a memory associated with the processor 612, but the entire program and/or parts thereof could alternatively be executed by a device other than the processor 612 and/or embodied in firmware or dedicated hardware. Further, although the example program is described with reference to the flowchart illustrated in FIG. 5, many other methods of implementing the example system 100 and/or components thereof illustrated in FIG. 1-3 may alternatively be used. For example, the order of execution of the blocks may be changed, and/or some of the blocks described may be changed, eliminated, or combined.

As mentioned above, the example process of FIG. 5 may be implemented using coded instructions (e.g., computer and/or machine readable instructions) stored on a tangible computer readable storage medium such as a hard disk drive, a flash memory, a read-only memory (ROM), a compact disk (CD), a digital versatile disk (DVD), a cache, a random-access memory (RAM) and/or any other storage device or storage disk in which information is stored for any duration (e.g., for extended time periods, permanently, for brief instances, for temporarily buffering, and/or for caching of the information). As used herein, the term tangible computer readable storage medium is expressly defined to include any type of computer readable storage device and/or storage disk and to exclude propagating signals and to exclude transmission media. As used herein, "tangible computer readable storage medium" and "tangible machine readable storage medium" are used interchangeably. Additionally or alternatively, the example process of FIG. 5 may be implemented using coded instructions (e.g., computer and/or machine readable instructions) stored on a non-transitory computer and/or machine readable medium such as a hard disk drive, a flash memory, a read-only memory, a compact disk, a digital versatile disk, a cache, a random-access memory and/or any other storage device or storage disk in which information is stored for any duration (e.g., for extended time periods, permanently, for brief instances, for temporarily buffering, and/or for caching of the information). As used herein, the term non-transitory computer readable medium is expressly defined to include any type of computer readable storage device and/or storage disk and to exclude propagating signals and to exclude transmission media. As used herein, when the phrase "at least" is used as the transition term in a preamble of a claim, it is open-ended in the same manner as the term "comprising" is open ended.

FIG. 5 is a flowchart representative of example machine-readable instructions that, when executed, may cause the example system 100 of FIGS. 1-3 to predict whether VR content (e.g., the VR content 204 of FIG. 2) is likely to induce a seizure (e.g., a PSE seizure) and/or other negative neurological and/or physiological response in a user (e.g., the user 104 of FIG. 1) and to dynamically modify the VR content to reduce the likelihood of the seizure and/or negative neurological/physiological response. In the example of FIG. 5, the VR content can be presented via the VR HMD 102 of FIG. 1 including the VR viewer 106 and/or the speaker(s) 108. The example instructions of FIG. 5 can be executed by the processing unit 112 of FIGS. 1-3.

The VR content monitor 210 of the example seizure monitor 116 retrieves a portion of the VR content 204 from the database 208 of the VR manager 114 of the example processing unit 112, such as the VR content stream 216 of FIG. 2 (block 500). The VR content monitor 210 scans the VR content stream 216 with respect to the video and/or audio parameters of the VR content stream 216. The video analyzer 212 generates one or more video vectors (e.g., the video vector(s) 218) with respect to video frames of the VR content stream 216 (block 502). The video vectors 218 can be generated based on, for example, analysis of data such as RGB pixel values of the respective frames. The video vectors can include data such as luminance, hue, and/or saturation values of the frame(s). In some examples, the audio analyzer 214 generates one or more audio vectors for audio synchronized with the video frames of the VR content stream 216. The audio vectors can include data such as decibel level(s) and/or pattern(s) in a frequency stream of audio stream(s) of the corresponding video frame(s).

The example neurological/physiological data collector 224 of the seizure monitor 116 of FIG. 2 accesses the neurological and/or physiological data 226 collected from the user exposed to the VR content 204 (block 504). The neurological/physiological data 226 is obtained from the user via the example sensors 110 of the VR HMD 102 of FIG. 1. The neurological and/or physiological data can include, for example, brain signal data (e.g., EEG data), galvanic skin response data, etc.

The example rules engine 222 of the seizure monitor 116 analyzes the video and/or audio vectors 218, 220 for the VR content stream 216 and the user's neurological/physiological data 226 based on one or more learned data algorithms (block 506). The rules engine 222 uses the learned data algorithm(s) (e.g., supervised learning algorithms) to identify seizure trigger content, or content that may induce a seizure (e.g., a PSE seizure) in one or more users. For example, the video vector analyzer 312 and/or the audio vector analyzer 314 of the example rules engine 222 compares the respective video and/or audio vectors 218, 220 generated for the VR content stream 216 to video and/or audio vectors (e.g., the calibration video and/or audio vectors 308, 310, the seizure trigger data 311 stored in the database 300) generated from VR content (e.g., the VR content 204 or other VR content) that previously induced a PSE seizure in one or more users (e.g., the user 104 and/or other users). The neurological/physiological data analyzer 304 of the rules engine 222 compares the neurological/physiological data 226 collected from the user in substantially real-time to neurological/physiological data collected from one or more users who previously experienced a PSE seizure (e.g., the calibration neurological/physiological data 302 stored in the database 300).

The video vector analyzer 312 and/or the audio vector analyzer 314 identify similarities and/or differences between the respective video and/or audio vectors 218, 220 of the VR content stream 216 and the learned data. The neurological/physiological data analyzer 304 analyzes the neurological/physiological data 226 collected from the user during exposure to the VR content 204 and the learned data. Based on the analysis with respect to the learned data, the predictor 316 of the rules engine 222 predicts whether the VR content stream 216 is likely to induce a seizure (e.g., a PSE seizure) in the user (block 508). Based on the learned data analysis, the predictor 316 may determine that the VR content stream 216 includes seizure trigger content and, thus, is likely to induce a seizure (e.g., a PSE seizure) and/or other neurological and/or physiological event in the user.

If a determination is made that the VR content stream 216 is likely to induce a seizure in the user (block 508), the content modification manager 318 of the example rules engine 222 determines one or modifications to the VR content stream 216, such as one or more modifications to the video and/or audio portions of the VR content stream 216. The content modification manager 318 generates one or more instructions 228 with respect to modification of the VR content stream 216. Based on the instruction(s) 228, the VR content modifier 230 of the example VR manager 114 modifies one or more visual and/or audio parameters of the VR content stream 216 to generate a modified VR content stream 232 in an attempt to reduce a likelihood of an occurrence of a seizure (e.g., a PSE seizure) in the user (block 510). The modifications performed by the VR content modifier 230 can include modifications with respect to hue and/or saturation values of one or more video frame(s) of the VR content stream 216, adjustments to the luminance (e.g., brightness) of the video frame(s), and/or a reduction in a decibel level of an audio stream played during presentation of the corresponding video frame(s). In some examples, the reduction of the decibel level of the audio stream includes muting the audio stream.

In some examples, if a determination is made that the VR content stream 216 is likely to induce a seizure in the user, the alert generator 320 of the example rules engine 222 determines that one or more alerts 234 should be provided to the user and/or to one or more third parties. The alert generator 320 can generate the alert(s) 236 for presentation via the VR viewer 106 and/or the speaker(s) 108 to recommend that the user turn off the VR content 204. In some examples, the alert generator 320 determines that the alert(s) 234 should be sent to a third party designated by the user to be notified when the rules engine 222 determines that the user is or is likely to experience a seizure (e.g., a PSE seizure).

The VR content modifier 230 transmits the modified VR content stream 232 for presentation to the user via the VR viewer 106 and/or the speaker(s) 108 (block 512). The modified VR content stream 216 can replace the VR content is to be presented to the user. In examples where the predictor 316 determines that the VR content stream 216 is not likely to induce a seizure (e.g., a PSE seizure) based on the learned data analysis (block 508), the VR content modifier 230 transmits the unmodified VR content stream 216 for presentation to the user via the VR viewer 106 and/or the speaker(s).

The example VR content modifier 230 transmits the presented content (e.g., the unmodified VR content stream 216 or the modified VR content stream 232) to the VR content monitor 210 for substantially continuous monitoring of the user's neurological and/physiological reaction to the VR content 204 to determine if, for example, the modification(s) to the VR content stream 216 successfully mitigated the likelihood of a seizure (e.g., a PSE seizure). The VR content modifier 230 generates the video and/or audio vectors 218, 220 for the modified VR content stream 232. Also, the neurological/physiological data collector 224 collects neurological/physiological data 226 from the user while the user is exposed to the modified VR content stream 232 or the unmodified VR content stream 216. The feedback analyzer 322 of the example rules engine 222 analyzes the neurological/physiological data 226 collected from the user while the user is exposed to the modified VR content stream 232 in view of the video and/or audio vectors 218, 220 for the presented content (e.g., the unmodified VR content stream 216 or the modified VR content stream 232) to evaluate the user's response to the presented content (block 514).

Based on the analysis of the neurological/physiological data 226 collected from the user while the user is exposed to the modified VR content stream 232 or the unmodified VR content stream 216, the rules engine 222 determines if additional modifications to the VR content 204 are appropriate. The VR content monitor 210 determines if there is another portion of the VR content 204 to be analyzed (e.g., a VR content stream 216 that is to be presented subsequent to the VR content stream 216 that was previously analyzed) (block 516). Based on the neurological/physiological data 226 collected from the user while the user is exposed to the modified VR content stream 232 or the unmodified VR content stream 216 (and other factors such as the visual/audio parameters of the next portion of the VR content 204), the rules engine 222 predicts whether the next portion of the VR content 204 includes seizure trigger content that is likely to induce a seizure (e.g., a PSE seizure) and/or other negative neurological/physiological event in the user and modifies the next portion for presentation accordingly (e.g., blocks 504-512).

If there are no additional portions of the VR content 204 to be analyzed, the instructions of FIG. 5 end (block 518). Also, if the content modification manager 318 determines that the VR content 204 should no longer be displayed to the user (e.g., if the neurological/physiological data 226 includes features indicative of a seizure (e.g., increased frequency of spikes in the data)), then the instructions of FIG. 5 end.

Figure 6:
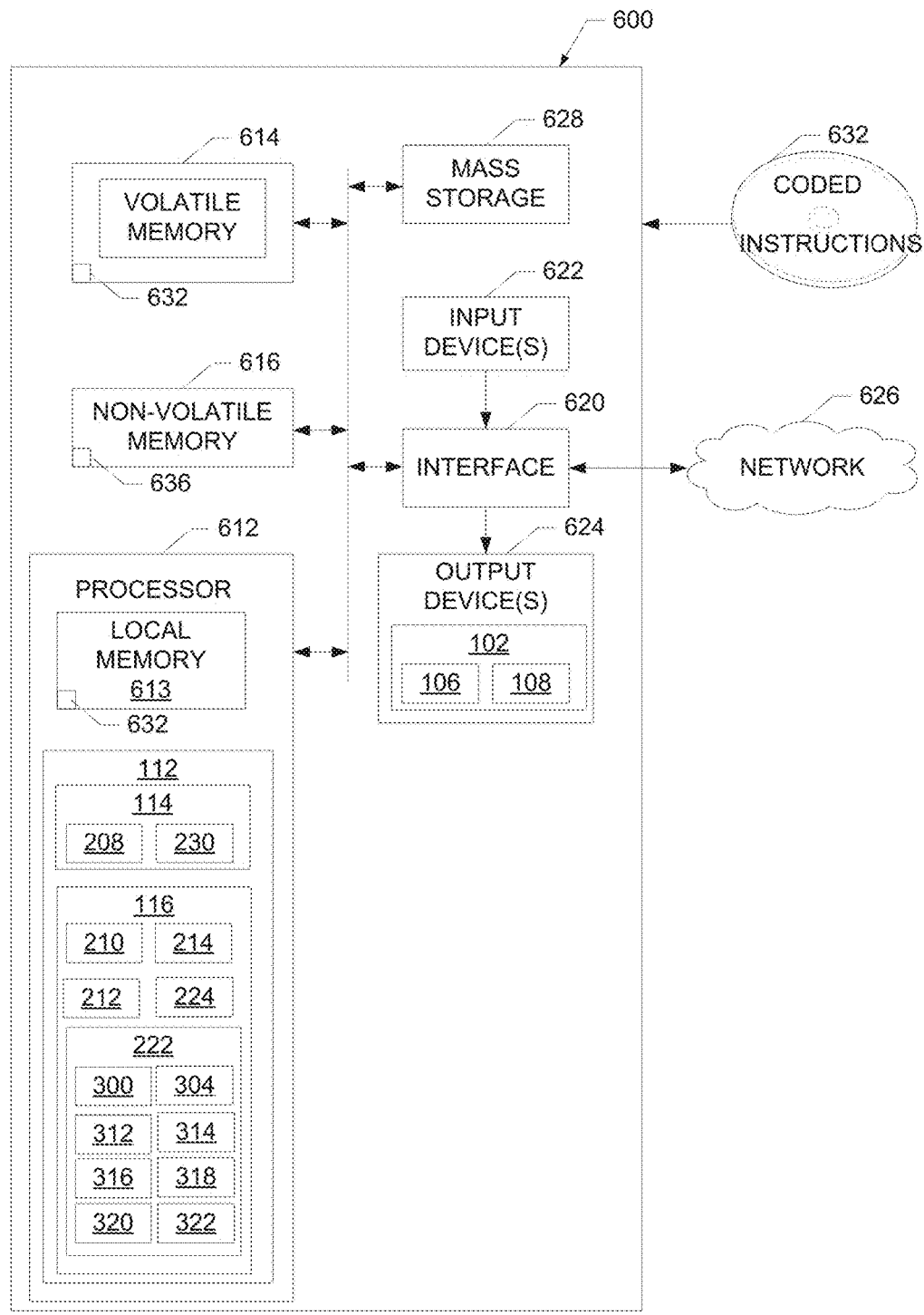
FIG. 6 illustrates an example processor platform that may execute the example instructions of FIG. 5 to implement the example systems of FIGS. 1-3.

FIG. 6 is a block diagram of an example processor platform 600 capable of executing the instructions of FIG. 5 to implement the example VR HMD 102, the example VR viewer 106, the example processing unit 112, the example VR manager 114, the example seizure monitor 116, the example databases 208, 300, the example VR content monitor 210, the example video analyzer 212, the example audio analyzer 214, the example rules engine 222, the example neurological/physiological data collector 224, the example VR content modifier 230, the example alert receiver 236, the example neurological/physiological data analyzer 304, the example video vector analyzer 312, the example audio vector analyzer 314, the example predictor 316, the example content modification manager 318, the example alert generator 320, the example feedback analyzer 322, and/or, more generally, the example system 100 of FIGS. 1-3. The processor platform 600 can be, for example, a server, a personal computer, a mobile device (e.g., a cell phone, a smart phone, a tablet such as an iPad™), a personal digital assistant (PDA), an Internet appliance a set top box, a headset, a VR presenter device, or a VR wearable device such as goggles or glasses, or any other type of computing device.

The processor platform 600 of the illustrated example includes a processor 612. The processor 612 of the illustrated example is hardware. For example, the processor 612 can be implemented by one or more integrated circuits, logic circuits, microprocessors or controllers from any desired family or manufacturer.

The processor 612 of the illustrated example includes a local memory 613 (e.g., a cache). The processor 612 of the illustrated example is in communication with a main memory including a volatile memory 614 and a non-volatile memory 616 via a bus 618. The volatile memory 614 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 616 may be implemented by flash memory and/or any other desired type of memory device. Access to the main memory 614, 616 is controlled by a memory controller.

The processor platform 600 of the illustrated example also includes an interface circuit 620. The interface circuit 620 may be implemented by any type of interface standard, such as an Ethernet interface, a universal serial bus (USB), and/or a PCI express interface.

In the illustrated example, one or more input devices 622 are connected to the interface circuit 620. The input device(s) 622 permit(s) a user to enter data and commands into the processor 612. The input device(s) can be implemented by, for example, an audio sensor, a microphone, a camera (still or video), a keyboard, a button, a mouse, a touchscreen, a track-pad, a trackball, isopoint and/or a voice recognition system.

One or more output devices 624 are also connected to the interface circuit 620 of the illustrated example. The output devices 624 can be implemented, for example, by display devices (e.g., a light emitting diode (LED), an organic light emitting diode (OLED), a liquid crystal display, a cathode ray tube display (CRT), a touchscreen, a tactile output device, a printer and/or speakers). The interface circuit 620 of the illustrated example, thus, typically includes a graphics driver card, a graphics driver chip or a graphics driver processor.

The interface circuit 620 of the illustrated example also includes a communication device such as a transmitter, a receiver, a transceiver, a modem and/or network interface card to facilitate exchange of data with external machines (e.g., computing devices of any kind) via a network 626 (e.g., an Ethernet connection, a digital subscriber line (DSL), a telephone line, coaxial cable, a cellular telephone system, etc.).

The processor platform 600 of the illustrated example also includes one or more mass storage devices 628 for storing software and/or data. Examples of such mass storage devices 628 include floppy disk drives, hard drive disks, compact disk drives, Blu-ray disk drives, RAID systems, and digital versatile disk (DVD) drives.

Coded instructions 632 to implement the instructions of FIG. 5 may be stored in the mass storage device 628, in the volatile memory 614, in the non-volatile memory 616, and/or on a removable tangible computer readable storage medium such as a CD or DVD.

From the foregoing, it will be appreciated that methods, systems, and apparatus have been disclosed to predict whether VR content is likely to induce a seizure (e.g., a PSE seizure) and/or other negative neurological and/or physiological responses in a user of a VR HMD. Disclosed examples use learned data with respect to seizure triggers to efficiently predict whether VR content is likely to induce a seizure (e.g., a PSE seizure) based on one or more visual and/or audio parameters of the VR content and the user's neurological response data. If a determination is made that the user is likely to experience a seizure and/or other negative neurological and/or physiological event while exposed to the VR content, the examples disclosed herein dynamically modify the VR content and transmit the modified VR content for presentation to the user. Thus, the examples disclosed address seizure inducing triggers in the VR content rather than simply displaying a general warning that the VR content may cause seizures in some individuals.

Disclosed examples also provide for continued monitoring of the user's response to the modified VR content to determine if further corrective actions are required, such as cutting off presentation of the VR content if the user experiences a seizure (e.g., a PSE seizure). Disclosed examples learn from the feedback to enhance the classification of the VR content and seizure trigger predictions. Thus, disclosed examples intelligently respond to the effects of the VR content on the user to mitigate the risks of seizures in a user exposed to VR content.

Although certain example methods, apparatus and articles of manufacture have been disclosed herein, the scope of coverage of this patent is not limited thereto. On the contrary, this patent covers all methods, apparatus and articles of manufacture fairly falling within the scope of the claims of this patent.

Further examples and combinations thereof include the following.

Example 1 is an apparatus for analyzing virtual reality content, comprising a virtual reality presentation device to display the virtual reality content for exposure to a user; a neurological data collector to access first neurological response data collected from the user during exposure to the virtual reality content; a predictor to generate a prediction on a likelihood that a portion of the virtual reality content will trigger a seizure based on a first vector characterizing the portion and the first neurological response data; a content modifier to modify the portion of the virtual reality content into modified virtual reality content in response to the prediction, the content modifier to transmit the modified virtual reality content to the virtual reality presentation device.

Example 2 includes the apparatus as defined in example 1, further including a video analyzer to generate the first vector based on a visual parameter of the portion of the virtual reality content.

Example 3 includes the apparatus as defined in example 1, wherein the predictor is to determine the likelihood that the portion of the virtual reality content will trigger the seizure based on a second vector and second neurological response data, the second vector and the second neurological response data associated with a second portion of the virtual reality content presented prior to the presentation of the portion of the virtual reality content.

Example 4 includes the apparatus as defined in example 1, wherein the portion of the virtual reality content includes a plurality of video frames and the content modifier is to modify the portion of the virtual reality content by adjusting at least one of a saturation value, a hue value, or a luminance of at least one of the video frames.

Example 5 includes the apparatus as defined in example 1, wherein the neurological data collector is to collect second neurological response data from the user, the second neurological response data collected during presentation of the modified virtual reality content, and further including a feedback analyzer, the feedback analyzer to determine a modification for the modified virtual reality content based on the second neurological response data.

Example 6 includes the apparatus as defined in example 5, wherein the content modifier is to stop a transmission of the virtual reality content based on the second neurological response data.

Example 7 includes the apparatus as defined in example 5, wherein the portion of the virtual reality content is a first portion and further including a content monitor to retrieve a second portion of the virtual reality content, the predictor to generate a prediction on a likelihood that the second portion will trigger a seizure in the user based on a second vector characterizing the second portion of the virtual reality content and the second neurological response data.

Example 8 includes the apparatus as defined in example 1, further including an alert generator to generate an alert based on the prediction.

Example 9 includes the apparatus as defined in example 8, wherein the alert generator is to transmit the alert to the virtual reality presentation device.

Example 10 includes the apparatus as defined in any of examples 1-9, wherein the first neurological response data includes electroencephalogy data.

Example 11 includes the apparatus as defined in any of examples 1-9, wherein the virtual reality presentation device further includes a speaker.

Example 12 includes the apparatus as defined in example 11, wherein the portion of the virtual reality content includes an audio stream and the content modifier is to modify the portion of the virtual reality content by reducing a decibel level of the audio stream.

Example 13 is a method for analyzing virtual reality content comprising accessing, by executing an instruction with at least one processor, first neurological data collected from a user during exposure of the user to the virtual reality content; generating, by executing an instruction with the at least one processor, a prediction on a likelihood that a portion of the virtual reality content will trigger a seizure based on a first vector characterizing the portion of the virtual reality content and first neurological response data; modifying, by executing an instruction with the at least one processor, the portion of the virtual reality content to generate modified virtual reality content in response to the prediction; and transmitting, by executing an instruction with the at least one processor, the modified virtual reality content to a virtual reality presentation device.

Example 14 includes the method as defined in example 13, further including generating the first vector based on a visual parameter or an audio parameter of the portion of the virtual reality content.

Example 15 includes the method as defined in example 13, wherein the generating of the prediction is further based on a second vector and second neurological response data, the second vector and the second neurological response data associated with a second portion of the virtual reality content presented prior to the presentation of the portion of the virtual reality content.

Example 16 includes the method as defined in example 13, wherein the portion of the virtual reality content includes a plurality of video frames and the modifying of the portion of the virtual reality content includes adjusting at least one of a saturation value, a hue value, or a luminance of at least one of the video frames.

Example 17 includes the method as defined in example 16, further including accessing second neurological response data collected during presentation of the modified virtual reality content; and modifying the modified virtual reality content based on the second neurological data.

Example 18 includes the method as defined in example 17, wherein the modifying the modified virtual reality content includes stopping a transmission of the virtual reality content.

Example 19 includes the method as defined in example 17, wherein the portion of the virtual reality content is a first portion and further including: retrieving a second portion of the virtual reality content; and generating a prediction on a likelihood that the second portion will trigger a seizure in the user based on a second vector characterizing the second portion of the virtual reality content and the second neurological response data.

Example 20 includes the method as defined in example 13, further including generating an alert based on the prediction.

Example 21 includes the method as defined in example 20, further including transmitting the alert to the virtual reality presentation device.

Example 22 includes the method as defined in any of examples 20 or 21, further including transmitting the alert to a mobile device.

Example 23 includes the method as defined in any of examples 13-22, wherein the generating of the prediction is based on a learned data algorithm.

Example 24 includes the method as defined in any of examples 13-23, wherein the generating of the prediction is further based on user profile data.

Example 25 includes the method as defined in example 24, wherein the user profile data includes one or more of an age of the user, a gender of the user, or a medical history of the user.

Example 26 includes the method of any of examples 13-25, wherein the first neurological response data includes electroencephalogy data.

Example 27 is a computer readable storage medium comprising instructions that, when executed, cause a machine to at least access first neurological data collected from a user during exposure of the user to virtual reality content; generate a prediction on a likelihood that the virtual reality content will trigger a seizure based on a first vector characterizing the virtual reality content and the first neurological response data; modify at least a portion of the virtual reality content to generate modified virtual reality content in response to the prediction; and transmit the modified virtual reality content to a virtual reality presentation device.

Example 28 includes the computer readable storage medium of example 27, wherein the instructions, when executed, further cause the machine to generate the first vector based on a visual parameter or an audio parameter of the virtual reality content.

Example 29 includes the computer readable storage medium of example 27, wherein the instructions, when executed, further cause the machine to generate the prediction based on a second vector and second neurological response data, the second vector and the second neurological response data associated with earlier presented virtual reality content.

Example 30 includes the computer readable storage medium of example 27, wherein the virtual reality content includes a plurality of video frames, and the instructions, when executed, further cause the machine to modify the virtual reality content by adjusting at least one of a saturation value, a hue value, or a luminance of at least one of the frames.

Example 31 includes the computer readable storage medium of example 27, wherein the instructions, when executed, further cause the machine to access second neurological response data collected during presentation the modified virtual reality content and to modify the modified virtual reality content based on the second neurological data.

Example 32 includes the computer readable storage medium of example 31, wherein the instructions, when executed, further cause the machine to stop a transmission of the virtual reality content.

Example 33 includes the computer readable storage medium of example 31, wherein the portion of the virtual reality content is a first portion and wherein the instructions, when executed, further cause the machine to: retrieve a second portion of the virtual reality content; and generate a prediction on a likelihood that the second portion will trigger a seizure in the user based on a second vector characterizing the second portion of the virtual reality content and the second neurological response data.

Example 34 includes the computer readable storage medium of example 27, wherein the instructions, when executed, further cause the machine to generate an alert based on the prediction.

Example 35 includes the computer readable storage medium of example 34, wherein the instructions, when executed, further cause the machine to transmit the alert to the virtual reality presentation device.

Example 36 includes the computer readable storage medium of any of examples 34 or 35, wherein the instructions, when executed, further cause the machine to transmit the alert to a mobile device.

Example 37 includes the computer readable storage medium of any of examples 27-36, wherein the first neurological response data includes electroencephalogy data.

Example 38 is an apparatus for analyzing virtual reality content comprising means for presenting the virtual reality content for exposure to a user; means for accessing first neurological data collected from a user during exposure of the user to the virtual reality content; means for generating a prediction on a likelihood that a portion of the virtual reality content will trigger a seizure based on a first vector characterizing the portion and the first neurological response data and means for modifying the portion of the virtual reality content into modified virtual reality content in response to the prediction, the means for modifying to transmit the modified virtual reality content to the means for presenting the virtual reality content.

Example 39 includes the apparatus of example 38, further including means for generating the first vector based on a visual parameter or an audio parameter of the portion of the virtual reality content.

Example 40 includes the apparatus of example 38, wherein the means for generating the prediction is to generate the prediction based on a second vector and second neurological response data, the second vector and the second neurological response data associated with a second portion of the virtual reality content presented prior to the presentation of the portion of the virtual reality content.

Example 41 includes the apparatus of example 38, wherein the portion of the virtual reality content includes a plurality of video frames and the means for modifying the portion includes means for adjusting at least one of a saturation value, a hue value, or a luminance of at least one of the video frames.

Example 42 includes the apparatus of example 38, wherein the means for accessing first neurological data is to access second neurological response data collected during presentation of the modified virtual reality content and wherein the means for modifying is to modify the modified virtual reality content based on the second neurological data.

Example 43 includes the apparatus of example 38, further including means for generating an alert based on the prediction.

Example 44 includes the apparatus of example 43, wherein the means for generating the alert is to transmit the alert to the means for presenting the virtual reality content.

Example 45 includes the apparatus of any of examples 43 or 44, wherein the means for generating the alert is to transmit the alert to a mobile device.

What is claimed is:

1. An apparatus for analyzing virtual reality content, the apparatus comprising:
    a virtual reality presentation device to display the virtual reality content for exposure to a user;
    a neurological data collector to access first neurological response data collected from the user during exposure to the virtual reality content;
    a predictor to generate a prediction on a likelihood that a portion of the virtual reality content will trigger a seizure based on a first vector characterizing the portion and the first neurological response data; and
    a content modifier to modify the portion of the virtual reality content into modified virtual reality content in response to the prediction, the content modifier to transmit the modified virtual reality content to the virtual reality presentation device.

2. The apparatus of claim 1, further including a video analyzer to generate the first vector based on a visual parameter of the portion of the virtual reality content.

3. The apparatus of claim 1, wherein the predictor is to further generate the prediction based on a second vector and second neurological response data, the second vector and the second neurological response data associated with a second portion of the virtual reality content presented prior to the presentation of the portion of the virtual reality content.

4. The apparatus of claim 1, wherein the portion of the virtual reality content includes a plurality of video frames and the content modifier is to modify the portion of the virtual reality content by adjusting at least one of a saturation value, a hue value, or a luminance of at least one of the video frames.

5. The apparatus of claim 1, wherein the neurological data collector is to access second neurological response data collected from the user, the second neurological response data collected during presentation of the modified virtual reality content, and further including a feedback analyzer, the feedback analyzer to determine a modification for the modified virtual reality content based on the second neurological response data.

6. The apparatus of claim 5, wherein the content modifier is to stop a transmission of the virtual reality content based on the second neurological response data.

7. The apparatus of claim 1, further including an alert generator to generate an alert based on the prediction.

8. A method for analyzing virtual reality content, the method comprising:
    accessing, by executing an instruction with at least one processor, first neurological data collected from a user during exposure of the user to the virtual reality content;
    generating, by executing an instruction with the at least one processor, a prediction on a likelihood that a portion of the virtual reality content will trigger a seizure based on a first vector characterizing the portion of the virtual reality content and first neurological response data;
    modifying, by executing an instruction with the at least one processor, the portion of the virtual reality content to generate modified virtual reality content in response to the prediction; and
    transmitting, by executing an instruction with the at least one processor, the modified virtual reality content to a virtual reality presentation device.

9. The method of claim 8, further including generating the first vector based on a visual parameter or an audio parameter of the portion of the virtual reality content.

10. The method of claim 8, wherein the generating of the prediction is further based on a second vector and second neurological response data, the second vector and the second neurological response data associated with a second portion of the virtual reality content presented prior to the presentation of the portion of the virtual reality content.

11. The method of claim 8, wherein the portion of the virtual reality content includes a plurality of video frames and the modifying of the portion of the virtual reality content includes adjusting at least one of a saturation value, a hue value, or a luminance of at least one of the video frames.

12. The method of claim 8, further including:
    accessing second neurological response data collected during presentation of the modified virtual reality content; and
    modifying the modified virtual reality content based on the second neurological data.

13. The method of claim 12, wherein the modifying of the modified virtual reality content includes stopping a transmission of the virtual reality content.

14. The method of claim 8, further including generating an alert based on the prediction.

15. A non-transitory computer readable storage medium comprising instructions that, when executed, cause a machine to at least:
    access first neurological data collected from a user during exposure of the user to virtual reality content;
    generate a prediction on a likelihood that the virtual reality content will trigger a seizure based on a first vector characterizing the virtual reality content and the first neurological response data;

modify at least a portion of the virtual reality content to generate modified virtual reality content in response to the prediction; and transmit the modified virtual reality content to a virtual reality presentation device.

16. The non-transitory computer readable storage medium of claim 15, wherein the instructions, when executed, further cause the machine to generate the first vector based on a visual parameter or an audio parameter of the virtual reality content.

17. The non-transitory computer readable storage medium of claim 15, wherein the instructions, when executed, further cause the machine to generate the prediction based on a second vector and second neurological response data, the second vector and the second neurological response data associated with earlier presented virtual reality content.

18. The non-transitory computer readable storage medium of claim 15, wherein the virtual reality content includes a plurality of video frames, and the instructions, when executed, further cause the machine to modify the at least the portion of the virtual reality content by adjusting at least one of a saturation value, a hue value, or a luminance of at least one of the frames.

19. The non-transitory computer readable storage medium of claim 18, wherein the instructions, when executed, further cause the machine to access second neurological response data collected during presentation of the modified virtual reality content and to modify the modified virtual reality content based on the second neurological data.

20. The non-transitory computer readable storage medium of claim 15, wherein the instructions, when executed, further cause the machine to generate an alert based on the prediction.

* * * * *